United States Patent [19]
Junge et al.

[11] Patent Number: 5,506,246
[45] Date of Patent: *Apr. 9, 1996

[54] METHOD FOR TREATING DEPRESSION USING SUBSTITUTED AMINOMETHYLTETRALINS AND THEIR HETEROCYCLIC ANALOGUES

[75] Inventors: Bodo Junge; Rudolf Schohe, both of Wuppertal; Peter-Rudolf Seidel, Cologne; Thomas Glaser, Roesrath; Jörg Traber, Lohmar; Ulrich Benz, Bergisch-Gladbach; Teunis Schuurman, Lohmar; Jean-Marie V. De Vry, Roesrath, all of Germany

[73] Assignee: Bayer Aktiengesellschaft, Leverkusen, Germany

[*] Notice: The portion of the term of this patent shall not extend beyond the expiration date of Pat. No. 5,137,901.

[21] Appl. No.: 171,941

[22] Filed: Dec. 21, 1993

Related U.S. Application Data

[60] Division of Ser. No. 864,853, Apr. 7, 1992, Pat. No. 5,300,523, which is a continuation-in-part of Ser. No. 378,732, Jul. 12, 1989, abandoned.

[30] Foreign Application Priority Data

Jul. 28, 1988 [DE] Germany .......................... 38 25 609.6
Jan. 23, 1989 [DE] Germany .......................... 39 01 814.8

[51] Int. Cl.$^6$ .................... C07D 417/00; A61K 31/425
[52] U.S. Cl. .................... 514/373; 514/372; 548/209; 548/210
[58] Field of Search .................... 514/456, 373, 514/372; 548/209, 210

[56] References Cited

U.S. PATENT DOCUMENTS

| | | | |
|---|---|---|---|
| 4,728,650 | 3/1988 | Eziri et al. | 549/407 |
| 4,748,182 | 5/1988 | Hibert et al. | 548/210 |
| 5,137,901 | 8/1992 | Junge et al. | 514/373 |
| 5,185,364 | 2/1993 | De Barnadis et al. | 514/456 |
| 5,364,857 | 11/1994 | Greuel | 514/373 |

FOREIGN PATENT DOCUMENTS 0236930  9/1987  European Pat. Off. .

OTHER PUBLICATIONS

Chemical Abstracts, vol. 118 (3):22144(j) 1992.
Chemical Abstracts, vol. 113(13):15087(c) (1990).

*Primary Examiner*—Nicholas Rizzo
*Attorney, Agent, or Firm*—Sprung Horn Kramer & Woods

[57] ABSTRACT

A method of treating depression or stroke in a patient suffering therefrom by administering a substituted aminomethylchroman of the formula in which Z—denotes a group of the formula and $R^1$, E and F can be hydrogen or other radicals, or salts thereof.

9 Claims, No Drawings

METHOD FOR TREATING DEPRESSION USING SUBSTITUTED AMINOMETHYLTETRALINS AND THEIR HETEROCYCLIC ANALOGUES

This is a division of application Ser. No. 07/864,953, filed Apr. 7, 1992, now U.S. Pat. No. 5,300,523, which is a continuation-in-part of application Ser. No. 07/378,732, filed Jul. 12, 1989, now abandoned.

The invention relates to substituted aminomethyltetralins and their heterocyclic analogues, processes for their preparation and their use in medicaments.

It is known that 2-N-dipropyl-amino-8-hydroxytetralin binds to central receptors of the 5-HT$_1$ type with high affinity and selectivity. It is further known that substituted aminomethylbenzodioxanes have a high affinity for receptors of the 5-HT$_1$ type and show an effect both on the cardiovascular and the central nervous system (EP-A 0,236, 930).

In addition, it is known that 3-aminochromans and 3-aminomethylchromans have a stimulating effect on the central nervous system (Ind. J. Chem., Sect. B. 21B (4), 344–347).

Substituted aminomethyltetralins and their heterocyclic analogues of the general formula

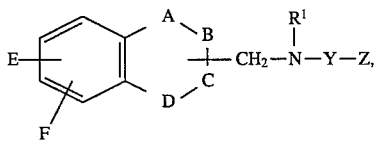

in which

Y—denotes a straight-chain or branched, saturated or unsaturated alkylene chain having up to 6 carbon atoms and Z—denotes a group of the formula

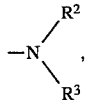

where

R$^7$ and R$^8$ are identical or different and represent hydrogen, alkyl, alkenyl, cycloalkyl, aryl or aralkyl, R$^2$ and R$^3$ are identical or different and represent hydrogen, alkyl, alkenyl or cycloalkyl, —represent aryl, aralkyl or heteroaryl, where the aryl and heteroaryl radicals may be optionally substituted by halogen, cyano, alkyl, alkoxy or trifluoromethyl, —represent a group of the formula

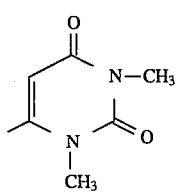

or

—represent a group of the formula —COR$^9$ or SO$_2$R$^{10}$, where

R$^9$—represents hydrogen or

—represents alkyl or alkoxy or

—represents aryl or aralkyl, which may optionally be monosubstituted to trisubstituted by identical or different alkyl, alkoxy, alkylthio, halogen, cyano, trifluoromethyl, trifluoromethoxy, trifluoromethylthio, amino, alkylamino or dialkylamino or —represents heteroaryl which may optionally be monosubstituted to trisubstituted by identical or different alkyl, alkoxy, alkylthio, halogen, cyano, trifluoromethyl, trifluoromethoxy, trifluoromethylthio, amino, alkylamino or dialkylamino or —represents a group NHR$^{11}$, R$^{11}$—represents alkyl which may optionally be substituted by cyano, halogen, trifluoromethyl or trifluoromethoxy or —represents aryl or aralkyl which may optionally be monosubstituted to trisubstituted by identical or different alkyl, alkoxy, alkylthio, halogen, cyano, trifluoromethyl, trifluoromethoxy, trifluoromethylthio, amino, alkylamino or dialkylamino R$^{10}$—represents alkyl which may optionally be substituted by cyano, halogen, alkoxycarbonyl, trifluoromethyl or trifluoromethoxy or represents aryl, aralkyl or heteroaryl, optionally monosubstituted to trisubstituted by identical or different alkyl, alkoxy, alkylthio, halogen, cyano, trifluoromethyl, trifluoromethoxy, trifluoromethylthio, amino, alkylamino or dialkylamino or represents a group of the formula

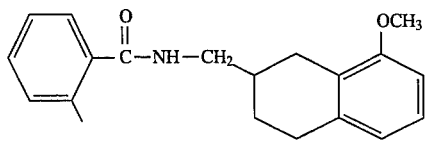

or

—represents a group of the formula —NR$^7$R$^8$, where

R$^7$ and R$^8$ have the abovementioned meaning, or

R$^2$ and R$^3$ together with the nitrogen atom form a heterocycle from the series comprising

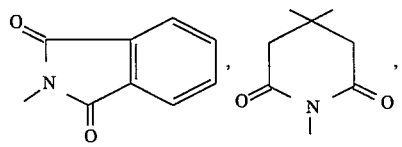

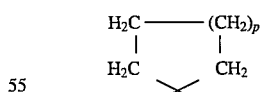

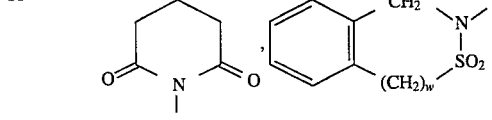

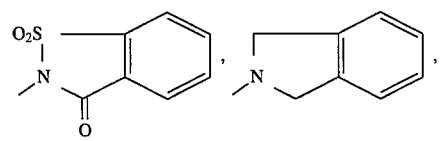

-continued

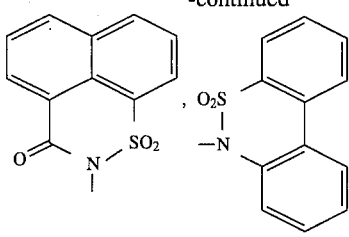, 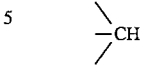

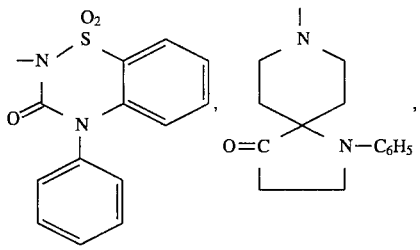

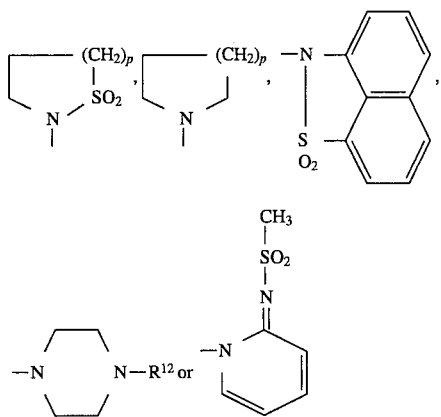

where
w—denotes the number 0, 1 or 2,
p—denotes the number 1 or 2,
$R^{12}$—represents acyl, alkoxycarbonyl, alkylsulphonyl, arylsulphonyl, aralkylsulphonyl, alkylarylsulphonyl, carbamoyl or sulphamoyl
$R^4$—represents hydrogen, alkyl or alkenyl or
—represents cycloalkyl or
—represents alkoxycarbonyl or
—represents aryloxycarbonyl or aralkoxycarbonyl,
$R^5$—represents alkyl, alkenyl or cycloalkyl or
—represents aryl or aralkyl, optionally monosubstituted to trisubstituted by identical or different halogen, cyano, alkyl, alkoxy, trifluoromethyl or trifluoromethoxy or
—represents a group of the formula —$NR^7R^8$ where $R^7$ and $R^8$ have the abovementioned meaning,
m—represents the number 0, 1 or 2,
$R^6$—represents hydrogen, alkyl, alkenyl, cycloalkyl, aryl or aralkyl,
$R^1$—denotes hydrogen, alkyl or aralkyl or
—denotes heteroarylalkyl or
—denotes the group —$(Y^1-Z^1)$, where $Y^1$ and $Z^1$ may be identical or different to Y and Z and have the abovementioned meaning of Y and Z.
A and D denote a group of the formula —$CH_2$, O, S, $NR^{13}$ or the —CH or N part of a C=C or C=N double bond, with the proviso that either only A or only D represents oxygen, sulphur or N—$R^{13}$, in which $R^{13}$—represents hydrogen, alkyl, alkoxy, acyl, alkoxycarbonyl or alkylsulphonyl,
B—denotes a group of the formula —$CH_2$—, $\begin{matrix} \diagdown \\ -CH \\ \diagup \end{matrix}$ or the CH or N part of a C=C or C=N double bond,
C—denotes a group of the formula $\begin{matrix} \diagdown \\ -CH \\ \diagup \end{matrix}$ or the C part of a C=C or C=N double bond
E and F are identical or different and
—denote hydrogen, alkyl, alkoxy, halogen, nitro, cyano, trifluoromethyl or trifluoromethoxy, or
—denote a group of the formula —$CONR^2R^3$
in which
$R^2$ and $R^3$ have the abovementioned meaning or
—E and F together form a saturated or unsaturated carbocycle having 6 carbon atoms,
and their salts have been found.

In the context of the present invention, the compounds according to the invention may have several asymmetric carbon atoms and therefore exist in various stereochemical forms. Moreover, compounds having a sulphoxide group may likewise exist in various stereochemical forms. The following isomeric forms of the substituted aminomethyltetralins and their heterocyclic analogues may be mentioned as examples.

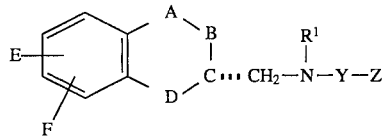

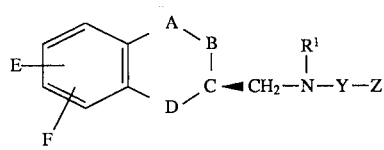

The compounds according to the invention may also exist in the form of their salts. In general, salts with inorganic or organic acids may be mentioned here.

In the context of the present invention physiologically acceptable salts are preferred.

Physiologically acceptable salts of the substituted aminomethyltetralins and their heterocyclic analogues may be salts of the substances according to the invention with mineral acids, carboxylic acids or sulphonic acids. For example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, oxalic acid, malonic acid, succinic acid, maleic acid, fumaric acid, malic acid, tartaric acid, citric acid or benzoic acid are particularly preferred.

The substances according to the invention surprisingly show an advantageous effect on the central nervous system and may be used for the therapeutic treatment of humans and animals. Compared to the already known structurally related compounds, they are distinguished by a greater selectivity for the 5-HT$_{1A}$ receptor owing to a partly serotonin-antagonistic effect and lower side-effects.

In the context of the present invention the substituents in general have the following meaning:

Alkyl in general represents a straight-chain or branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

Alkenyl in general represents a straight-chain or branched hydrocarbon radical having 2 to 12 carbon atoms and having one or more, preferably one or two, double bonds. The lower alkenyl radical having 2 to about 6 carbon atoms and a double bond is preferred. An alkenyl radical having 2 to 4 carbon atoms and a double bond is particularly preferred. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

Cycloalkyl in general represents a cyclic hydrocarbon radical having 5 to 8 carbon atoms. The cyclopentane ring and the cyclohexane ring are preferred. Examples which may be mentioned are cyclopentyl, cyclohexyl, cycloheptyl and cyclooctyl.

Aryl in general represents an aromatic radical having 6 to about 12 carbon atoms. Preferred aryl radicals are phenyl, naphthyl and biphenyl.

Akralkyl in general represents an aryl radical having 7 to 14 carbon atoms which is bonded via an alkylene chain. Aralkyl radicals having 1 to 6 carbon atoms in the aliphatic moiety and 6 to 12 carbon atoms in the aromatic moiety are preferred. Examples which may be mentioned are the following aralkyl radicals: benzyl, naphthylmethyl, phenethyl and phenylpropyl.

Alkoxy in general represents a straight-chain or branched hydrocarbon radical having 1 to 12 carbon atoms and bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

Alkylthio in general represents a straight-chain or branched hydrocarbon radical having 1 to 12 carbon atoms and bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio or isooctylthio.

Acyl in general represents phenyl or straight-chain or branched lower alkyl having 1 to about 6 carbon atoms which are bonded via a carbonyl group. Phenyl and alkyl radicals having up to 4 carbon atoms are preferred. Examples which may be mentioned are: benzoyl, acetyl, ethylcarbonyl, propylcarbonyl, isopropylcarbonyl, butylcarbonyl and isobutylcarbonyl.

Alkoxycarbonyl may be represented, for example, by the formula

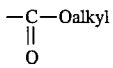

In this case, alkyl represents a straight-chain or branched hydrocarbon radical having 1 to 12 carbon atoms. Lower alkoxycarbonyl having.1 to about 6 carbon atoms in the alkyl moiety is preferred. An alkoxycarbonyl having 1 to 4 carbon atoms in the alkyl moiety is particularly preferred. Examples which may be mentioned are the following alkoxycarbonyl radicals: Methoxycarbonyl, ethoxycarbonyl, propoxycarbonyl, isopropoxycarbonyl, butoxycarbonyl or isobutoxycarbonyl.

Aryloxycarbonyl may be represented, for example, by the formula —COO-aryl. In this case, aryl in general represents an aromatic radical having 6 to 12 carbon atoms. Examples which may be mentioned are: phenoxycarbonyl and naphthyloxycarbonyl.

Aralkoxycarbonyl may be represented, for example, by the formula —COO-aralkyl. In this case, aralkyl in general represents an aryl radical having 7 to 14 carbon atoms and bonded via an alkylene chain, aralkyl radicals having 1 to 6 carbon atoms in the aliphatic moiety and 6 to 12 carbon atoms in the aromatic moiety being preferred. Examples which may be mentioned as aralkoxycarbonyl radicals are: benzyloxycarbonyl and naphthylmethyloxycarbonyl.

Heteroaryl in the context of the abovementioned definition in general represents a 5- to 6-membered aromatic ring which may contain oxygen, sulphur and/or nitrogen as heteroatoms and to which a further aromatic ring may be fused. 5- and 6-membered aromatic rings are preferred which contain an oxygen, a sulphur and/or up to 2 nitrogen atoms and which are optionally fused to benzene. Particularly preferred heteroaryl radicals which may be mentioned are:
thienyl, furyl, pyridyl, pyrimidyl, pyrazinyl, pyridazinyl, quinolyl, isoquinolyl, quinazolyl, quinoxalyl, thiazolyl, benzothiazolyl, isothiazolyl, oxazolyl, benzoxazolyl, isoxazolyl, imidazolyl, benzimidazolyl, pyrazolyl and indolyl.

Halogen in general represents fluorine, chlorine, bromine or iodine, preferably fluorine, chlorine or bromine. Halogen particularly preferably represents fluorine or chlorine.

Sulphamoyl (aminosulphonyl) represents the group —SO$_2$—NH$_2$.

Alkylsulphonyl in general represents a straight-chain or branched hydrocarbon radical having 1 to 12 carbon atoms which is bonded via an SO$_2$ group. Lower alkylsulphonyl having 1 to about 6 carbon atoms is preferred. Examples which may be mentioned are: methylsulphonyl, ethylsulphonyl, propylsulphonyl, isopropylsulphonyl, butylsulphonyl, isobutylsulphonyl, pentylsulphonyl, isopentulsulphonyl, hexysulphonyl and isohexylsulphonyl.

Arylsulphonyl in general represents an aromatic radical having 6 to about 12 carbon atoms which is bonded via an SO$_2$ group. Examples which may be mentioned are: phenylsulphonyl, napthylsulphonyl and biphenylsulphonyl, in particular phenylsulphonyl.

Aralkylsulphonyl in general represents an aralkyl radical having 7 to about 14 carbon atoms, the alkyl radical being bonded via an SO$_2$ chain. Aralkylsulphonyl radicals having 1 to 6 carbon atoms in the aliphatic moiety are preferred. Examples which may be mentioned are the following aralkysulphonyl radicals: benzylsulphonyl, napthylmethylsulphonyl, phenethylsulphonyl and phenylpropylsulphonyl, in particular benzylsulphonyl.

Preferred compounds of the general formula (I) are those in which

Y—denotes a straight-chain or branched, saturated or unsaturated alkylene chain having up to 6 carbon atoms
and
Z—denotes a group of the formula

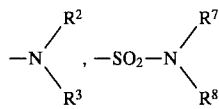

where
$R^7$ and $R^8$ are identical or different and
—represent hydrogen, lower alkyl, lower alkenyl, cycloalkyl, phenyl, benzyl or phenethyl
$R^2$ and $R^3$ are identical or different and
—represent hydrogen, lower alkyl or lower alkenyl or
—represent cycloalkyl or
—represent phenyl, benzyl or pyridyl which are optionally substituted by fluorine, chlorine, bromine, cyano, lower alkyl, lower alkoxy or trifluoromethyl or
—represent a group of the formula

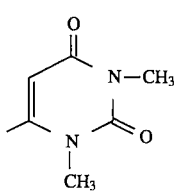

or
—represent a group of the formula —$COR^9$ or —$SO_2R^{10}$, in which
$R^9$—represents hydrogen or
represents lower alkyl or lower alkoxy or
represents phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl which may optionally be monosubstituted or disubstituted by lower alkyl, lower alkoxy, fluorine, chlorine, bromine, trifluoromethyl, dimethylamino or diethylamino or
—represents a group of the formula —$NHR^{11}$, where
$R^{11}$—represents lower alkyl which may optionally be substituted by cyano, fluorine, chlorine or bromine or
—represents phenyl, benzyl, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino,
$R^{10}$—represents lower alkyl which may optionally be substituted by cyano, fluorine, chlorine, bromine, trifluoromethyl or lower alkoxycarbonyl or
—represents phenyl, naphthyl, benzyl, thienyl, furyl, pyrimidyl, pyridyl, quinolyl, isoquinolyl, benzothiazolyl, benzoxazolyl, thiazolyl, oxazolyl, isoxazolyl or isothiazolyl, optionally monosubstituted or disubstituted by lower alkyl, lower alkoxy, fluorine, chlorine, bromine, trifluoromethyl, dimethylamino or diethylamino or —represents a group of the formula

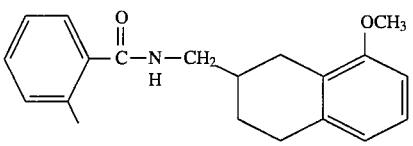

or
—represents a group of the formula $NR^7R^8$, where
$R^7$ and $R^8$ have the abovementioned meaning, or $R^2$ and $R^3$ together with the nitrogen atom form a heterocycle from the series comprising

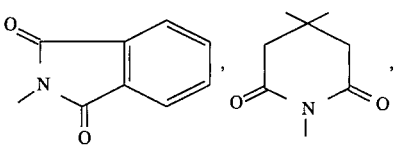

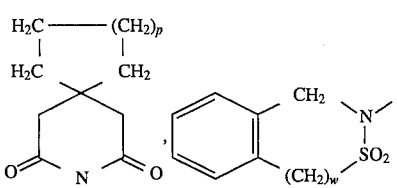

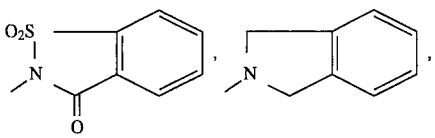

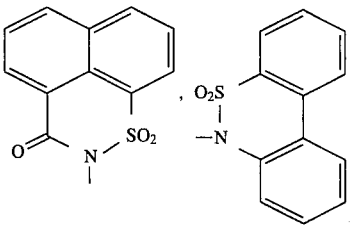

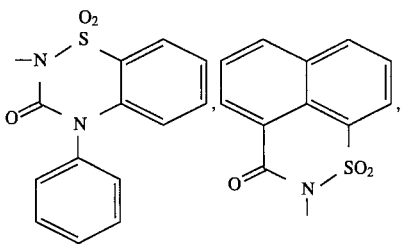

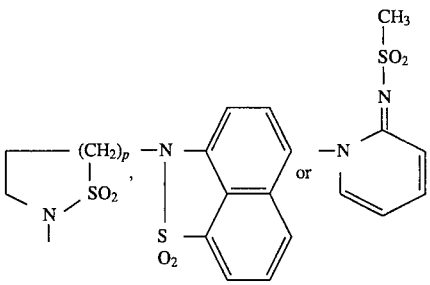

where
w—denotes a number 0, 1 or 2 p—denotes a number 1 or 2 and

R¹—denotes hydrogen, lower alkyl or benzyl or

—denotes the group —(Y¹-Z¹), where Y¹ and Z¹ may be identical or different to Y and Z and have the above-mentioned meaning of Y and Z A and D—may denote a group of the formula —CH₂, or oxygen, sulphur, NR¹³ or the CH or N part of a C═C or C═N double bond, with the proviso that either only A or only D can denote a group of the formula O, S or NR¹³ and in which R¹³—represents hydrogen, lower alkyl, lower alkoxy, lower alkoxycarbonyl or lower alkylsulphonyl B—denotes a group of the formula —CH₂—,

or denotes the CH part of a C═C or C═N double bond,

C—denotes a group of the formula

or the C part of a C═C or C═N double bond,

E and F are identical or different and

—denote hydrogen, lower alkyl or lower alkoxy or

—denote fluorine, chlorine, bromine, cyano or a group of the formula —CONR²R², where R² and R³ represent hydrogen or E and F together form a phenyl or cyclohexane ring, and their salts.

Particularly preferred compounds of the formula I are those in which

Y—denotes a straight-chain alkylene chain having 2–5 carbon atoms,

Z—denotes a group of the formula

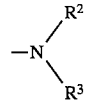

where

R² and R³ are identical or different and

—represent hydrogen, methyl, ethyl, propyl or

—represent phenyl, benzyl or pyridyl, which is optionally substituted by fluorine, chlorine, methyl or methoxy —represent a group of the formula

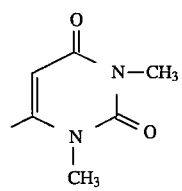

—represent a group of the formula —COR⁹ or —SO₂R¹⁰, in which

R⁹—represents methyl, ethyl or ethoxy or

—represents phenyl or benzyl, optionally substituted by methyl, methoxy, fluorine or chlorine R¹⁰—represents methyl, ethyl or propyl, or —represents phenyl, naphthyl or benzyl, which is optionally substituted by fluorine or chlorine or —represents a group of the formula

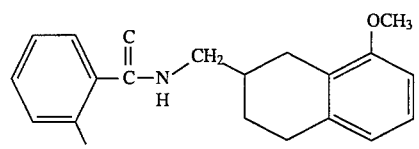

or

R² and R³ together with the nitrogen atom form a heterocycle from the series comprising

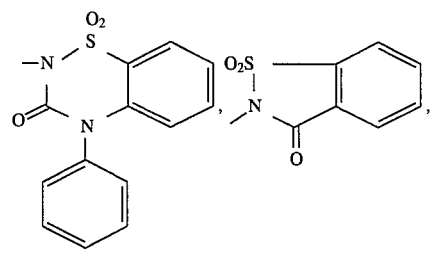

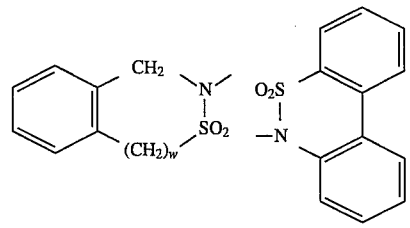

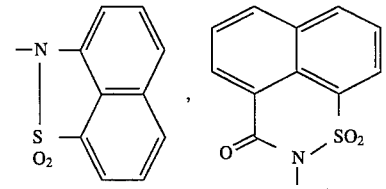

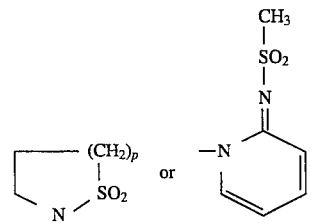

w—denotes a number 0, 1 or 2 p—denotes a number 1 or 2,

R¹— denotes hydrogen, ethyl, methyl, propyl or benzyl or denotes the group —(Y¹—Z¹), where Y¹ and Z¹ may be identical or different to Y and Z and have the above-mentioned meaning of Y and Z A and D denote a group of the formula —CH₂ or oxygen or the —CH or N part of a C═C or C═N double bond with the proviso that either only A or only D can denote oxygen, B—denotes a group of the formula

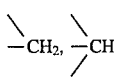

or denotes the CH part of a C=C or C=N double bond,
C—denotes a group of the formula

or the C part of a C=C or C=N double bond,
E and F are identical or different and represent hydrogen, ethoxy, methoxy, fluorine, cyano or a group of the formula —CONR$^2$R$^3$ where R$^2$ and R$^3$ represent hydrogen,
E and F together form a phenyl or cyclohexane ring, and their salts.

Very particularly preferred compounds of the formula I are those
in which
Y—denotes a straight-chain alkylene chain having 2–5 carbon atoms,
Z—denotes a group of the formula

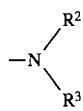

in which
R$^2$ and R$^3$ are identical or different and
—represent hydrogen, methyl, benzyl or pyridyl
—represent a group of the formula

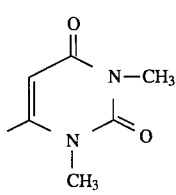

—represent a group of the formula —COR$^9$ or SO$_2$R$^{10}$, in which
R$^9$—represents phenyl or ethoxy
R$^{10}$—represents phenyl or naphthyl which may be substituted by fluorine or
—represents methyl
—represents a group of the formula

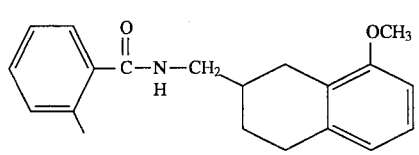

R$^2$ and R$^3$ together with the nitrogen atom form a hetero cycle of the formula

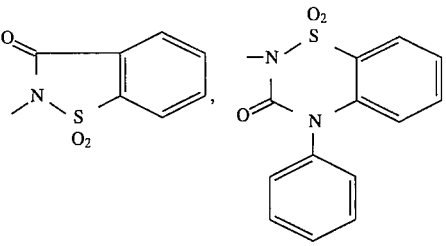

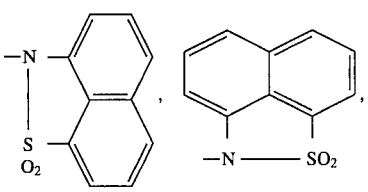

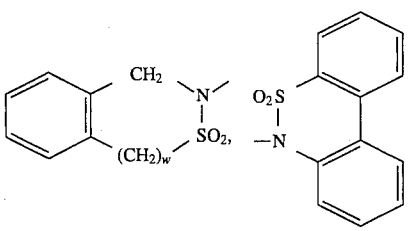

or

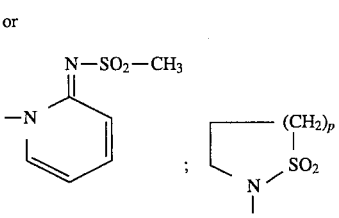

in which
w—denotes a number 0, 1 or 2 and
p—denotes a number 1 or 2,
R$^1$—denotes hydrogen, methyl, propyl or benzyl or
—denotes a group —(Y$^1$–Z$^1$), where Y$^1$ and Z$^1$ may be identical or different to Y and Z and have the abovementioned meaning of Y and Z
A and D denote a group of the formula

or oxygen or the —CH or N part of a C=C or C=N double bond with the proviso that either only A or only D can denote oxygen,
B—denotes a group of the formula

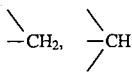

or denotes the CH part of a C=C or C=N double bond,

C—denotes a group of the formula

or the C part of a C=C or C=N double bond,

E and F are identical or different and represent hydrogen, ethoxy, methoxy, fluorine, cyano or a group of the formula —CONR²R³ where R² and R³ represent hydrogen, E and F together form a cyclohexane or phenyl ring, and their salts.

Processes for the preparation of the compounds of the general formula (I) according to the invention have furthermore been found, characterized in that [A] compounds of the general formula (II)

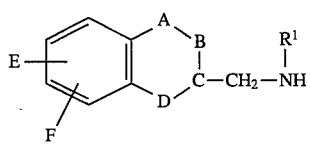

in which

A, B, Cm D, E, F and R¹ have the abovementioned meanings, (A1) are reacted with alkylating agents of the formula (III)

<p style="text-align:center">L—Y—Z    (III),</p> in which

Y and Z have the abovementioned meanings, with the provisos that

Z does not represent amino and

R² does not represent hydrogen if

R³ represents alkyl or aryl, and

L denotes a leaving group for alkylating agents or (A2) are reductively alkylated using aldehydes of the formula (IV)

    (IV), in which

Z has the abovementioned meaning and Y² is an alkylene chain Y shortened by one methylene group, or (A3) are reacted with reactive acid derivatives of the general formula (V)

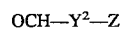    (V), in which

Y² and Z have the meanings indicated under process variant (A1) and M denotes a leaving group for acylating agents, and the corresponding acid amides are reduced using hydrogen in the presence of a catalyst, using boranes or using complex metal hydrides, or (A4) are alkylated with nitriles of the formula

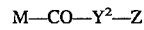

in which

G represents monochlorinated lower alkyl ($C_1$ to $C_3$), vinyl or lower alkyl ($C_1$ to $C_3$)- substituted vinyl, to give compounds of the formulae (VI) and (VII)

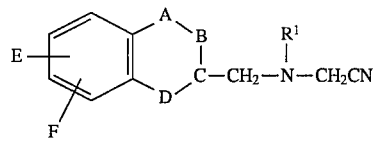

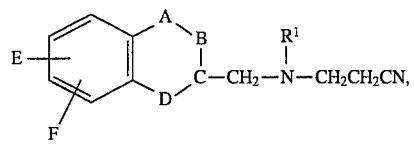

in which

A, B, C, D, E, F, and R¹ have the abovementioned meaning the nitriles obtained are hydrogenated to give the amines (VIII) and (IX)

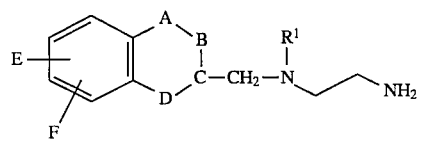

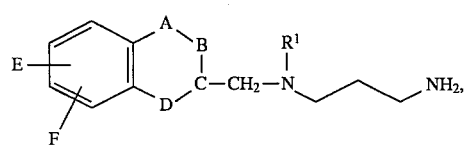

in which

A, B, C, D, E, F and R¹ have the abovementioned meaning, and these are reacted in a manner known per se by alkylation, reductive alkylation, acylation, reaction with isocyanates or sulphonylations, or in that

[B] compounds of the formula (X)

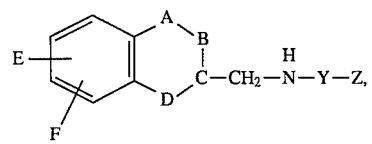

in which

A, B, C, D, E, F, Y and Z have the abovementioned meanings, with the provisos that Z does not represent amino and R² does not represent hydrogen if R³ represents alkyl or aryl, (B1) are alkylated using alkylating agents of the formula (XI)

—L    (XI), in which

R¹ has the abovementioned meaning and

L denotes a leaving group for alkylating agents, or (B2) by reductively alkylating with aldehydes of the formula (XII)

—CHO    (XII), in which R¹⁴ denotes a radical R¹ shortened by one methylene group, or (B3) are reacted with reactive acid derivatives of the general formula (XIII)

$$M-CO-R^{14} \quad (XIII)$$

in which $R^{14}$ has the abovementioned meaning and

M denotes a leaving group for acylating agents, and the corresponding acid amides are reduced using hydrogen in the presence of a catalyst or using complex metal hydrides,

[C] aldehydes of the formula (XIV)

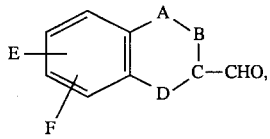

in which

A, B, C, D, E and F have the abovementioned meaning, are reductively aminated amines of the formula (XV), (XVI) or (XVII)

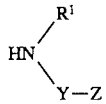

$$H_2N-R^1 \quad (XVI)$$

$$H_2N-Y-Z \quad (XVII)$$

in which $R^1$, Y and Z have the abovementioned meanings with the provisos that

Z does not represent amino and $R^2$ does not represent hydrogen if $R^3$ represents alkyl or aryl, in a manner known per se, or in that

[D] compounds of the general formula (XVIII)

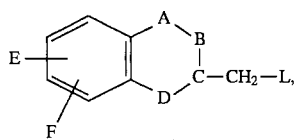

in which

A, B, C, D, E and F and X have the abovementioned meanings and

L denotes a leaving group for alkylating agents, are reacted with amines of the formulae

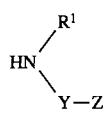

$$H_2N-R^1 \quad (XVI)$$

$$H_2N-Y-Z, \quad (XVII)$$

in which $R^1$, Y and Z have the abovementioned meanings with the provisos that

Z does not represent amino and $R^2$ does not represent hydrogen if $R^3$ represents alkyl or aryl, or are reacted with an alkali metal azide and subsequently the azido function is reduced to an amino function, or in that

[E] reactive carboxylic acid derivatives of the formula (XIX)

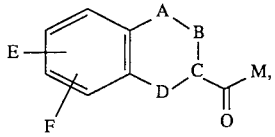

in which

A, B, C, D, S and F have the abovementioned meaning, and

M denotes a leaving group for acylating agents, are reacted with amines of the formulae

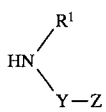

$$H_2N-R^1 \quad (XVI)$$

$$H_2N-Y-Z, \quad (XVII)$$

in which $R^1$, Y and Z have the abovementioned meanings, with the provisos that Z does not represent amino and $R^2$ does not represent hydrogen if $R^3$ represents alkyl or aryl, and the amides thus obtained of the formulae (XX) and (XXI)

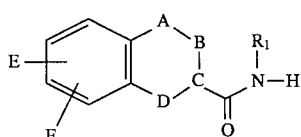

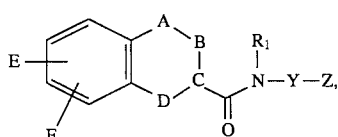

in which

A, B, C, D, E, F, $R^1$, Y and Z have the abovementioned meanings, are catalytically reduced using hydrogen, using complex metal hydrides or using boranes, or in that

[F] compounds of the general formula (XXII)

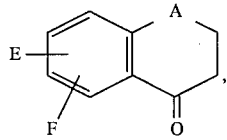

in which A, E and F have the abovementioned meaning are reacted with formaldehyde and amines of the formula (XV)

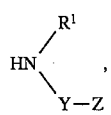
(XV)

in which
R[1], Y and Z have the abovementioned meanings
with the provisos that
Z does not represent amino and
R[2] does not represent hydrogen if
R[3] represents alkyl or aryl,
and the intermediates obtained of the general formula (XXIII)

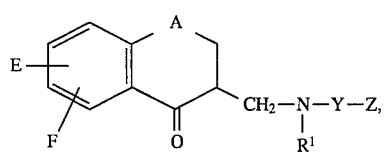
(XXIII)

in which
A, E, F, R[1], Y and Z have the abovementioned meanings, are further reacted by reduction of the carbonyl function or by partial reduction of the carbonyl function to the alcohol function, subsequent elimination of water and, if desired, hydrogenation of the C=C double bond using hydrogen.

The equations below illustrate the processes for the preparation of the compounds of the general formula I according to the invention:

Process A:
Variant A1:

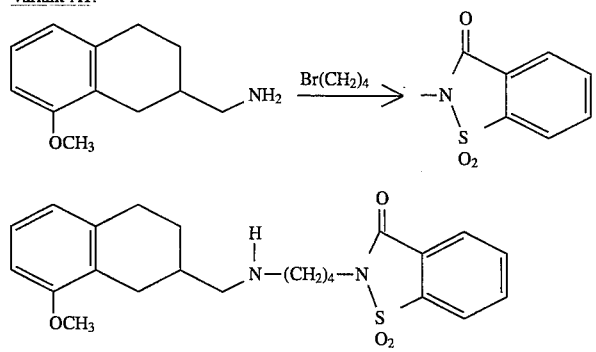

Variant A2:

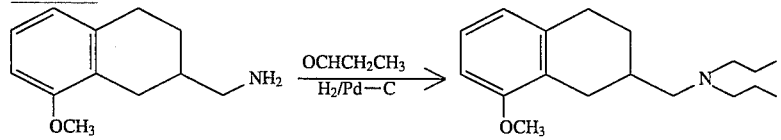

Variant A3:

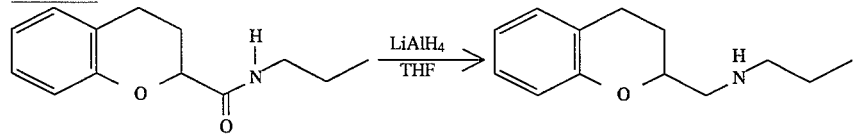

Variant A4:

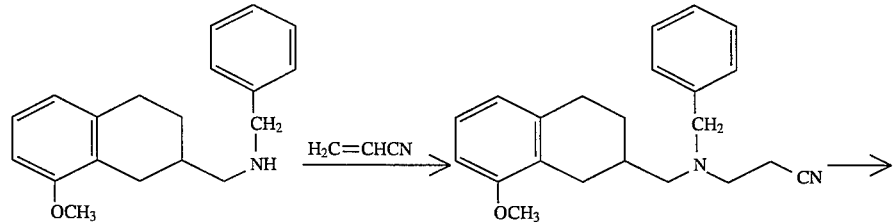

-continued
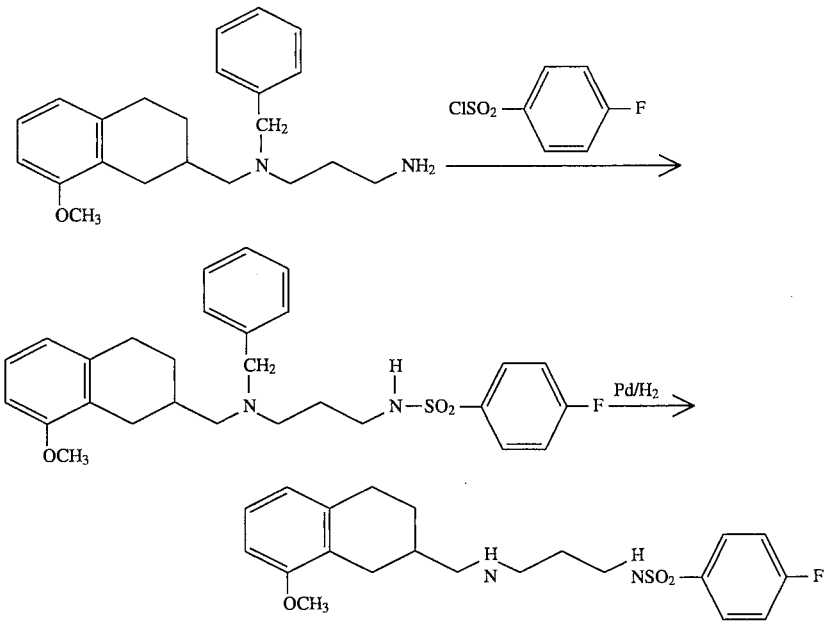
Process B:
Variant B1:
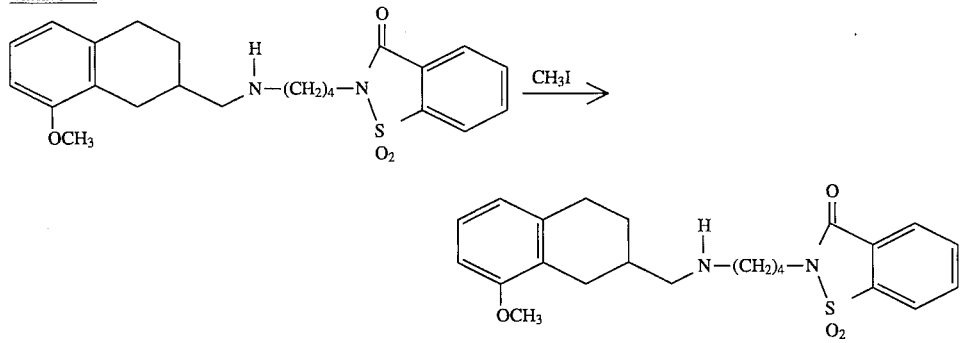
Variant B2:
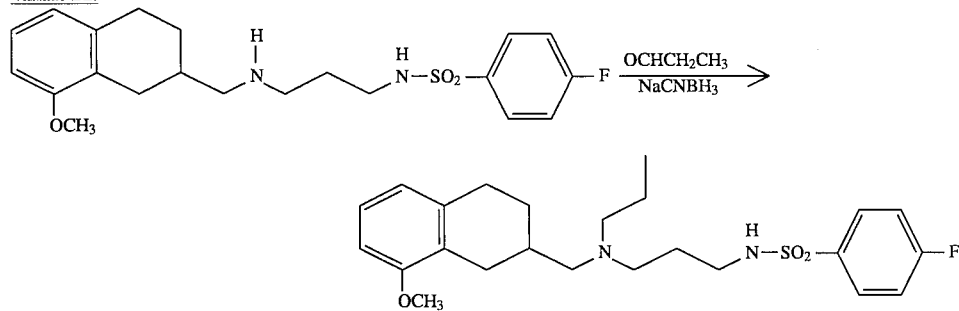
Variant B3:
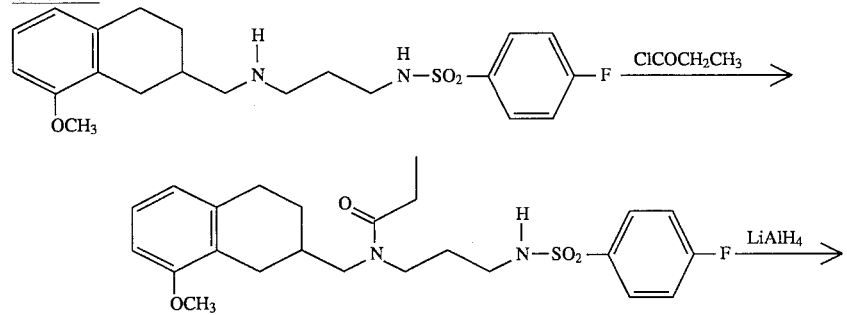

-continued
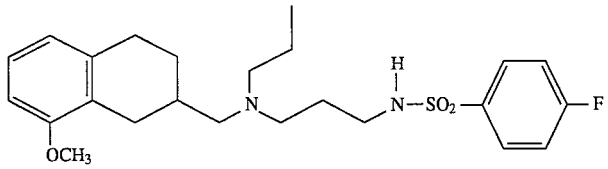
Process C:
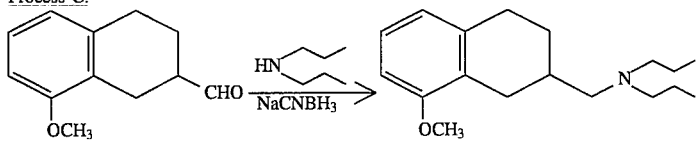
Process D:
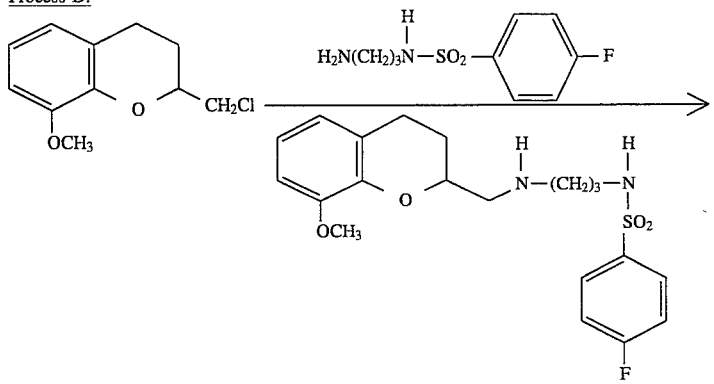
Process E:
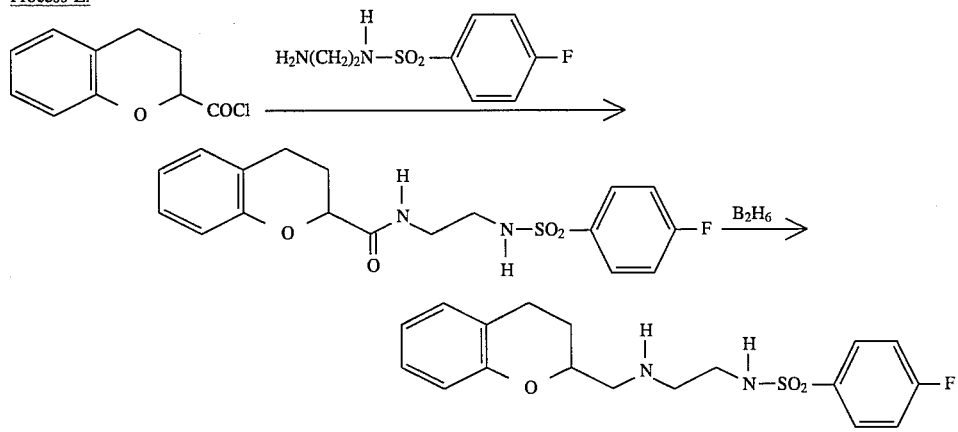
Process F:
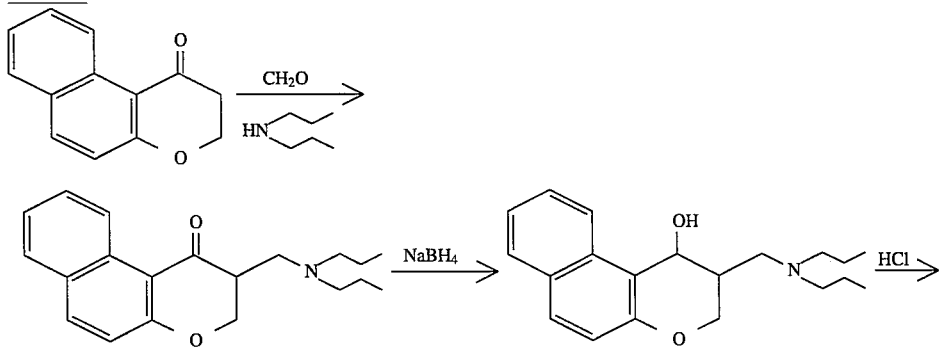

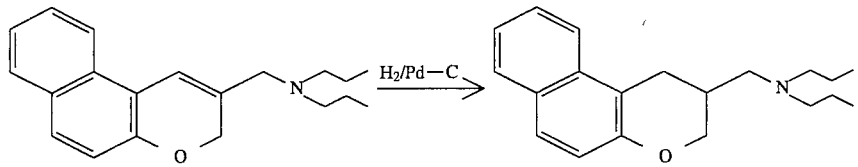

The amines of the formulae (II) and (X) used as starting materials are known per se and can be prepared in a manner known per se from the corresponding ketones by reductive amination, alkylation or reductive alkylation (compare GB 1,043,857, J. Med. Chem. 29, 1619, 1968, J. Med. Chem. 11, 844 (1968), EP-A 0,192,288). P. A. Robins, J. Walev, J. Chem. Soc. 1958, 409, J. Chem. Soc. 1942, 689).

Solvents which can be used here for the reaction of the &mines (II) and (X) with the alkylating agents (III) and (XI) are the customary organic solvents which do not change under the reaction conditions. These preferably include alcohols such as methanol, ethanol, propanol or isopropanol, or ethers such as diethyl ether, dioxane, tetrahydrofuran, glycol dimethyl ether or butyl methyl ether, or ketones such as acetone or butanone, or amides such as dimethylformamide or hexamethylphosphoramide, or dimethyl sulphoxide, acetonitrile, ethyl acetate or halogenated hydrocarbons such as methylene chloride, chloroform or carbon tetrachloride, or pyridine, picoline or N-methylpiperidine. Mixtures of the solvents mentioned can also be used.

Suitable bases are the customary inorganic or organic bases. These preferably include alkali metal hydroxides such as, for example, sodium hydroxide or potassium hydroxide, or alkali metal carbonates such as sodium carbonate or potassium carbonate, or alkali metal alkoxides such as, for example, sodium methoxide or potassium methoxide, or sodium ethoxide or potassium ethoxide, or organic amines such as triethylamine, picoline or N-methylpiperidine, or amides such as sodium amide or lithium diisopropylamide, or organometallic compounds such as butyllithium or phenyllithium.

Leaving groups for alkylating agents (L) are known per se (Lit. H. R. Christen, Grundlagen der organischen Chemie (Fundamentals of Organic Chemistry) Sauerländer-Diesterweg-Salle 1975). For example, chlorine, bromine, iodine, tosylate, mesylate or the group $-OSO_2CF_3$ may be mentioned here.

Leaving groups for acylating agents (M) are known per se (Lit. H. R. Christen, Grundlagen der organischen Chemie (Fundamentals of Organic Chemistry), Sauerländer-Diesterweg-Salle 1975). For example, chlorine, bromine, alkoxy($C_1$ to $C_4$), aryloxy, imidazolyl, thiazolyl, methanesulphonyloxy or alkoxy($C_1$ to $C_4$)carbonyl may be mentioned here.

The reaction is in general carried out in a temperature range from 0° C. to +150° C., preferably in a range from room temperature to +80° C.

The reaction is in general carried out at atmospheric pressure. However it is also possible to carry out the reaction at elevated or reduced pressure.

Reaction accelerators employed are in general alkali metal iodides, sodium iodide or potassium iodide being preferred.

In this connection, the base is employed in an amount from 1 to 5, preferably from 1 to 2, moles relative to 1 mole of the halogen compound. The halogen compound is preferably employed in up to a 10-fold, preferably in up to a 5-fold, excess amount over the compounds of the formula (II) or (X).

The reductive alkylation of the amines (II) and (X) with the aldehydes (IV) and (XII) is in general carried out in one step. If the amine (II) is a primary amine, the reaction can also be carried out in two steps, a Schiff's base or an enamine being obtained first.

The preparation of the Schiff's bases or enamines in the first step is carried out in inert organic solvents, if appropriate in the presence of a catalyst and if appropriate in the presence of a water-binding agent. The process according to the invention may be carried out in two steps, i.e. with isolation of the intermediates. It is also possible to carry out the reduction as a one-pot process.

In this connection, suitable inert solvents are the customary organic solvents which do not change under the reaction conditions. These preferably include alcohols such as methanol, ethanol, propanol or isopropanol, or ethers such as diethyl ether, butyl methyl ether, dioxane, tetrahydrofuran, glycol dimethyl ether or diethylene glycol diethyl ether, or halogenated hydrocarbons such as, for example, methylene chloride, chloroform or carbon tetrachloride, or hydrocarbons such as benzene, toluene, xylene, or mineral oil fractions, or amides such as dimethylformamide or hexamethylphosphoramide or acetic acid. In addition, it is possible to use mixtures of the solvents mentioned.

Protonic acids are in general used as catalysts. These preferably include inorganic acids such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or having aryl radicals such as, for example, methanesulphonic acid, ethanesulphonic acid, benzenesulphonic acid or toluenesulphonic acid.

The water formed in the reaction may optionally be removed during or after the reaction mixed with the solvent used, for example by distillation or by addition of water-binding agents, such as, for example, phosphorus pentoxide or preferably by molecular sieve.

The reaction is in general carried out in a temperature range from 0° C. to 150° C., preferably from +20° C. to +100° C.

The reaction can be carried out at normal, elevated and at reduced pressure (for example 0.5–5 bar). In general, the reaction is carried out at atmospheric pressure.

When carrying out the reaction, the compound (XV) is employed in an amount from 0.1–10, preferably from 0.5–5, moles relative to 1 mole of the compounds (II) or (X).

The reduction of the Schiff's bases or enamines in the second step is carried out either by means of hydrogen in water or in inert organic solvents such as alcohols, ethers or halogenated hydrocarbons, or their mixtures, using catalysts such as Raney nickel, palladium, palladium on animal charcoal or platinum, or using hydrides in inert solvents, if appropriate in the presence of a catalyst.

Preferably, the reaction is carried out using hydrides, such as complex borohydrides or aluminum hydrides. Sodium borohydride, lithium aluminum hydride or sodium cyanoborohydride are particularly preferably employed in this connection.

Suitable solvents in this connection are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether or aides such as hexamethylphosphoramide or dimethylformamide, or acetic acid. It is also possible to use mixtures of the solvents mentioned.

Protonic acids are in general used as catalysts in the reduction with sodium cyanoborohydride. These preferably include inorganic acids such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or having aryl radicals such as, for example, methanesulphonic acid, ethanesulphonic acid, benzenesulphonic acid or toluenesulphonic acid.

When carrying out the process according to the invention, it has proved favorable to carry out the reaction of the aldehydes (IV) and (XII) with the amines (II) and (X) in an inert solvent, preferably in acetic acid or alcohols, such as, for example, methanol, ethanol, propanol or isopropanol or their mixtures, in the presence of inorganic or organic acids such as, for example, hydrochloric acid or acetic acid, and in the presence of a reducing agent, preferably of complex hydrides such as, for example, sodium borohydride or sodium cyanoborohydride, if appropriate in the presence of a dehydrating agent, preferably molecular sieve, as a one-pot process.

In this case, the reaction is carried out in a temperature range from 0° C. to +150° C., preferably from 0° C. to +100° C. at atmospheric pressure. It is also possible to carry out the reaction at subatmospheric pressure or at excess pressure (for example in a bomb tube).

The conversion of functional groups into other functional groups in the abovementioned preparation processes is carried out, depending on the functional groups, by oxidation, reduction, hydrolysis or by reaction with electrophilic reagents and is illustrated in the following.

1. The reduction of the nitrile group to the amino group is in general carried out using metal hydrides, preferably using lithium aluminum hydride, aluminum hydride (prepared, for example, by reaction of lithium aluminum hydride with 100% strength sulphuric acid or with aluminum chloride) or their mixtures in inert solvents such as ethers or chlorinated hydrocarbons, preferably in ethers such as, for example, tetrahydrofuran, diethyl ether or dioxane in a temperature range from –20° C. to 100° C., preferably from 0° C. to +50° C., at atmospheric pressure.

The reduction is additionally possible by hydrogenating the nitriles in inert solvents such as alcohols, for example methanol, ethanol, propanol or isopropanol in the presence of a noble metal catalyst such as platinum, palladium, palladium on animal charcoal or Raney nickel, in a temperature range from 0° C. to +150° C., preferably from room temperature to +100° C., at atmospheric pressure or at excess pressure.

The reaction can be illustrated by the following equation:

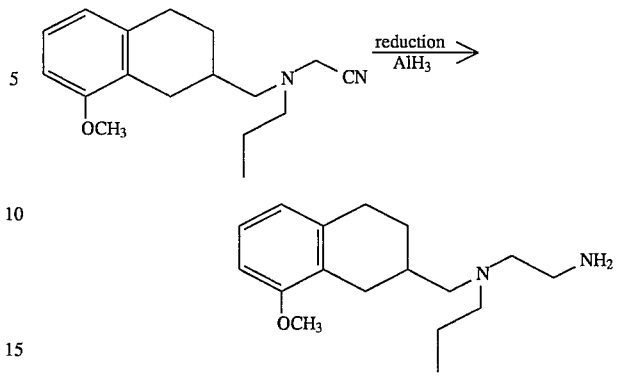

2. The reduction of alkoxycarbonyl groups to alcohol groups is in general carried out using hydrides, preferably using lithium aluminum hydride in inert solvents such as ethers, hydrocarbons or halogenated hydrocarbons or their mixtures, preferably in ethers such as, for example, diethyl ether, tetrahydrofuran or dioxane in a temperature range from 0° C. to +150° C., preferably from +20° C. to +100° C., at atmospheric pressure.

The reaction can be illustrated by the following equation:

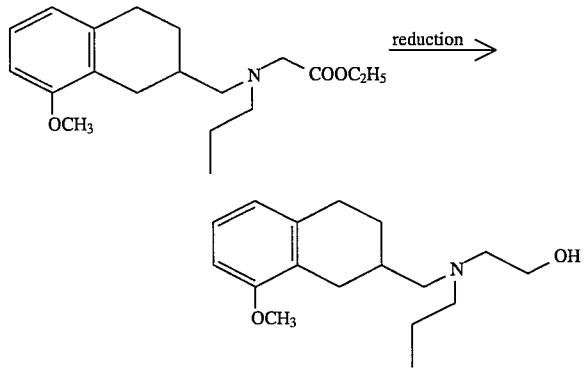

3. The hydrolysis of the nitrile group to the carboxamide group is in general carried out with the aid of strong mineral acids, preferably with hydrogen chloride in inert solvents such as water and/or alcohols such as, for example, methanol, ethanol, propanol or isopropanol in a temperature range from 0° C. to +150° C., preferably from +20° C. to +100° C., at atmospheric pressure.

The reaction can be illustrated by the following equation:

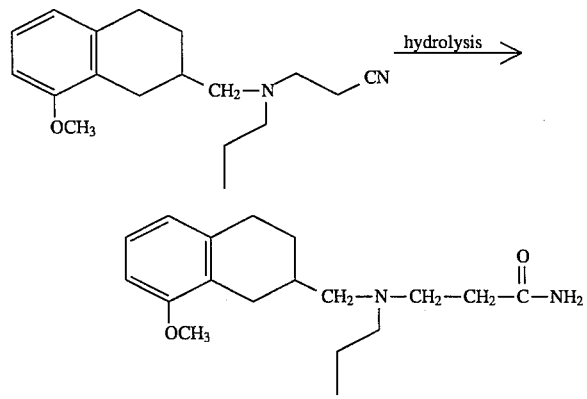

4. A large number of additional compounds according to the invention are obtained by reaction of NH— or OH— acidic compounds (Z in formula (I) is $NR^2R^3$, where $R^2$=H and $R^3$=H, alkyl, aryl or aralkyl), with electrophilic reagents:

a) The conversion of amines to carboxamides is in general carried out by reaction with carboxylic acid esters in inert solvents such as ethers or their mixtures or hydrocarbons, preferably in ethers such as, for example, diethyl ether, tetrahydrofuran or dioxane, if appropriate in the presence of bases such as alkali metals, alkali metal hydrides, alkali metal alkoxides or organolithium compounds, preferably in the presence of alkali metals, such as, for example, sodium or alkali metal hydrides such as sodium hydride or potassium hydride in a temperature range from +20° C. to +150° C., preferably at the boiling point of the solvent used and at atmospheric pressure.

Moreover, it is possible to prepare the amides using carboxylic acid halides or anhydrides, preferably using carboxylic acid chlorides in inert solvents such as ethers, hydrocarbons or halogenated hydrocarbons or their mixtures, preferably in ethers such as, for example, diethyl ether, tetrahydrofuran, or halogenated hydrocarbons such as methylene chloride or chloroform, if appropriate in the presence of bases such as alkali metal carbonates, for example sodium carbonate or potassium carbonate, or organic amines such as, for example, triethylamine or pyridine, in a temperature range from –20° C. to +100° C., preferably from 0° C. to +60° C., at atmospheric pressure.

The reaction can be illustrated by the following equation:

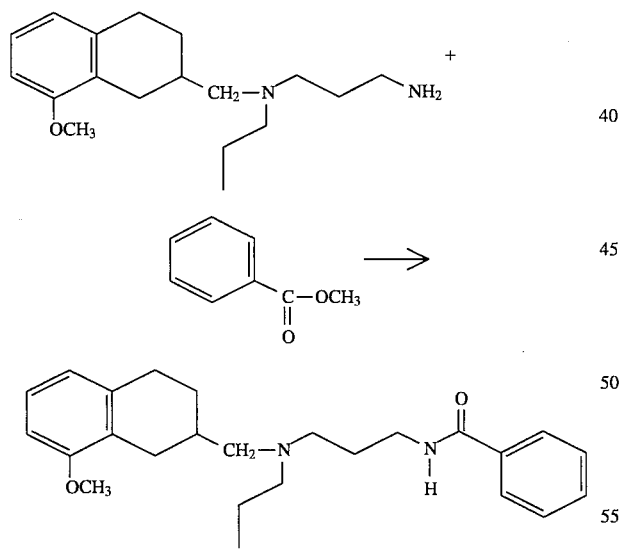

b) The conversion of amines to carbamates is in general carried out using carbonic acid esters, preferably using carbonic acid esters which carry a phenyl ester radical or using chlorocarbonic acid esters, in inert solvents such as ethers, hydrocarbons or halogenated hydrocarbons or their mixtures, preferably in ethers such as, for example, diethyl ether, tetrahydrofuran or dioxane, in a temperature range from +20° C. to +150° C., preferably from +20° C. to +100° C., at atmospheric pressure. The reaction can also be carried out in a two-phase system, the aqueous phase containing an auxiliary base such as sodium carbonate or potassium carbonate or sodium hydrogen carbonate or potassium hydrogen carbonate.

The reaction can be illustrated by the following equation:

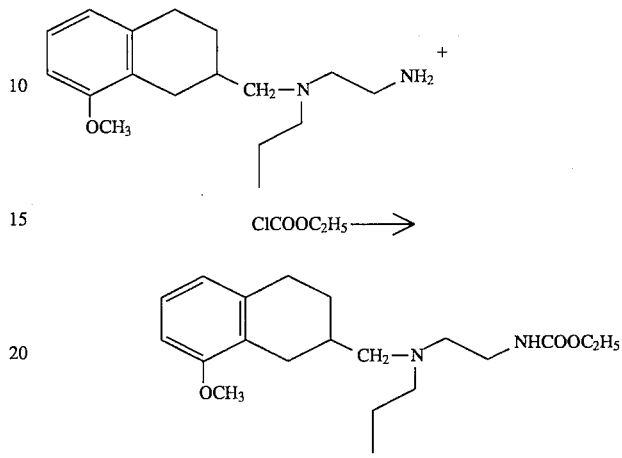

c) The conversion of amines into ureas is in general carried out by reaction with isocyanates in inert solvents such as ethers, hydrocarbons or halogenated hydrocarbons or their mixtures, preferably in ethers such as, for example, diethyl ether or tetrahydrofuran, or in halogenated hydrocarbons such as, for example, methylene chloride or chloroform, in a temperature range from –20° C. to +150° C., preferably from 0° C. to +100° C., at atmospheric pressure.

The reaction can be illustrated by the following equation:

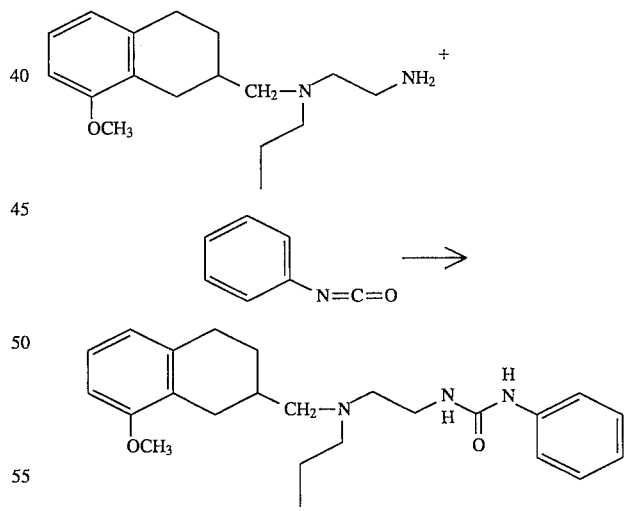

d) The conversion of amines to sulphonamides or aminosulphamoyl derivatives is in general carried out using sulphonyl halides or using amidosulphonyl halides, preferably using the corresponding chlorides in inert solvents such as ethers, hydrocarbons or halogenated hydrocarbons or their mixtures, preferably in halogenated hydrocarbons such as, for example, methylene chloride or chloroform, if appropriate in the presence of bases such as alkali metal hydroxides, alkali metal carbonates, alkali metal alkoxides or organic amines, preferably using alkali metal hydroxides such as sodium hydroxide or potassium hydroxide, alkali metal carbonates such as, for example, sodium carbonate or potassium carbonate, or organic amines such as triethylamine or pyridine, in a temperature range from −20° C. to +100° C., preferably from 0° C. to +50° C. at atmospheric pressure.

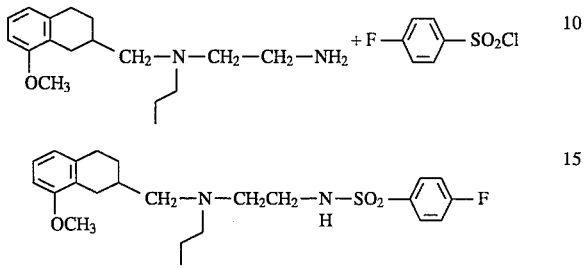

e) Cyclic sulphonamides are in general
prepared by reaction of intramolecular electrophiles in inert dipolar aprotic solvents, preferably in dimethylformamide, hexamethylphosphoramide or dimethyl sulphoxide, if appropriate in the presence of bases such as alkali metals, alkali metal hydrides, alkali metal amides, alkali metal alkoxides or organolithium compounds, preferably in the presence of alkali metal hydrides such as sodium hydride or potassium hydride, or alkali metal amides such as sodium amide or lithium diisopropylamide, if appropriate in the presence of catalytic amounts of an alkali metal iodide, for example sodium iodide or potassium iodide in a temperature range from −20° C. to +100° C., preferably from 0° C. to +50° C., at atmospheric pressure.

The reaction can be illustrated by the following equation:

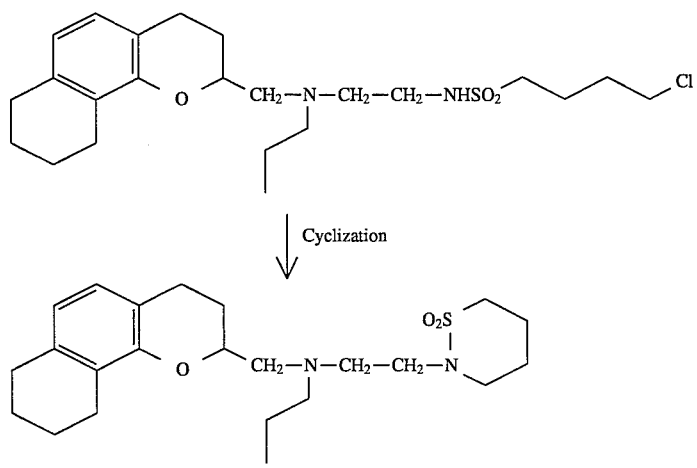

pyridine, picoline or dimethylaminopyridines in a temperature range from −20° C. to +100° C., preferably from 0° C. to room temperature at atmospheric pressure.

The reaction can be illustrated by the following equation:

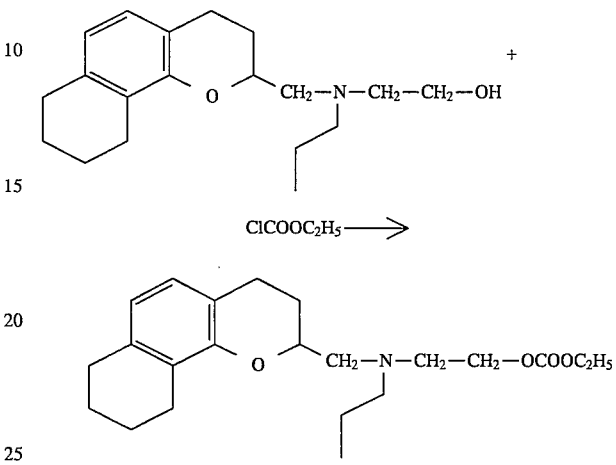

5. The oxidation of the thioether group to sulphoxides or sulphones is in general carried out using oxidizing agents such as peroxo compounds or hydrogen peroxide itself, preferably using hydrogen peroxide, in inert solvents such as carboxylic acids and carboxylic acid anhydrides, preferably in acetic acid, in a temperature range from −20° C. to +100° C., preferably from 0° C. to +50° C.

f) The conversion of the hydroxyl group to a carbonic acid ester is in general carried out by reacting with haloformic acid esters, preferably using chloroformic acid esters in inert solvents such as ethers, hydrocarbons or halogenated hydrocarbons, preferably in halogenated hydrocarbons such as methylene chloride or chloroform, or in ethers such as diethyl ether or tetrahydrofuran, if appropriate in the presence of bases such as alkali metal hydroxides, alkali metal carbonates or organic amines, preferably in the presence of organic amines such as triethylamine, The reaction can be illustrated by the following equation:

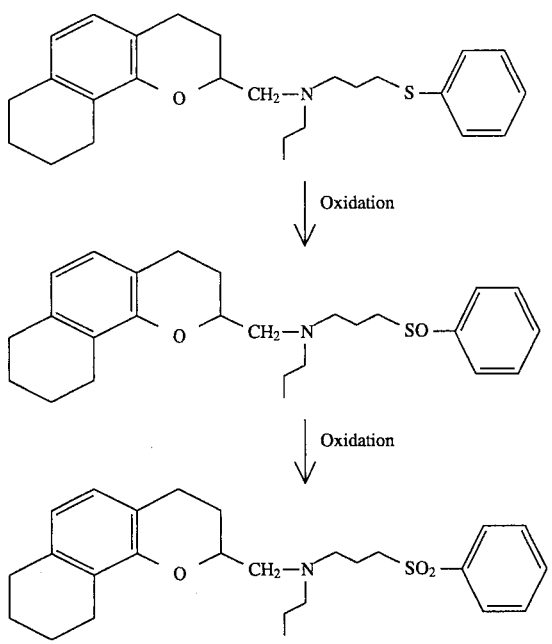

The amines of the general formula (XV), (XVI) and (XVII) employed as starting materials are known or can be prepared by known methods [Houben-Weyl's "Methoden der organischen Chemie" ("Methods of Organic Chemistry") volume XI/1 and XI/2).

Amines which can be used, for example, according to the invention are: ammonia, methylamine, ethylamine, propylamine, isopropylamine, butylamine, 4-dimethylaminobutylamine, 4-diethylaminobutylamine, 3-dimethylaminopropylamine, 3-diethylaminopropylamine, 2-dimethylaminoethylamine, 2-diethylaminoethylamine, 2-amino-1-ethoxycarbonytamidoethane, 3-amino-1-ethoxycarbonylamidopropane, 4-amino-1-ethoxycarbonylamidobutane, 3-aminoquinuclidine, 2-[(phenylaminocarbonyl)amino]ethylamine, 2-[(phenylaminocarbonyl)amino]propylamine, 4-aminomethylpiperidine, 4-(ethorycarbonyl)aminoethylpiperidine, N-methylpiperazine, 4-amino-1-carboxyethylpiperidine, N,N-dimethylpropylidenediamine, N,N-diethylpropylidenediamine, N,N-diethylethylidenediamine, N,N-dimethylethylenediamine, N-(2-aminoethyl)ethyl carbamate or N-(2-aminoethyl)propyl carbamate.

The reactions of the compounds of the general formula (XIX), (XXII) and (XIV) are carried out using amines of the general formula (XV), (XVI) and (XVII) in inert organic solvents, if appropriate in the presence of a catalyst and if appropriate in the presence of water-binding agents.

Suitable inert solvents in this connection are the customary organic solvents which do not change under the reaction conditions. These preferably include alcohols such as methanol, ethanol, propanol or isopropanol, or ethers such as diethyl ether, butyl methyl ether, dioxane, tetrahydrofuran, glycol dimethyl ether or diethylene glycol dimethyl ether, or halogenated hydrocarbons such as, for example, methylene chloride, chloroform or carbon tetrachloride, or hydrocarbons such as benzene, toluene, xylene, or mineral oil fractions, or amides such as dimethylformamide or hexamethylphosphoramide, or acetic acid. In addition it is possible to use mixtures of the solvents mentioned.

Acids are in general used as catalysts. These preferably include inorganic acids such as, for example, hydrochloric acid or sulphuric acid, or organic sulphonic or carboxylic acids such as, for example, methanesulphonic acid, ethanesulphonic acid, benzenesulphonic acid, toluenesulphonic acid, acetic acid or propionic acid.

The water formed in the reaction can optionally be removed during or after the reaction mixed with the solvent used, for example by distillation or by addition of water-binding agents, such as, for example, phosphorus pentoxide or preferably by molecular sieve.

The reactions are in general carried out in a temperature range from 0° C. to +150° C., preferably from 20° C. to +100° C.

The reaction can be carried out at atmospheric, elevated or at reduced pressure (for example 0.5–5 bar). In general, the reaction is carried out at atmospheric pressure.

The reductions of the compounds of the formulae (XX), (XXI) and (XXIII) are carried out either by means of hydrogen in water or inert organic solvents such as alcohols, ethers or halogenated hydrocarbons, or their mixtures, using catalysts such as Raney nickel, palladium, palladium on animal charcoal or platinum, or else using hydrides in inert solvents, if appropriate in the presence of a catalyst.

The reactions are preferably carried out using hydrides, such as complex borohydrides or aluminum hydrides. Sodium borohydride, lithium aluminum hydride, sodium cyanoborohydride or hydroboric acid are particularly preferably employed in this connection.

Suitable solvents in this connection are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, or amides such as hexamethylphosphoramide, or dimethylformamide or acetic acid. It is also possible to use mixtures of the solvents mentioned.

Acids are in general used as catalysts in the reduction with sodium cyanoborohydride. These preferably include inorganic acids such as, for example, hydrochloric acid or sulphuric acid or organic carboxylic acids or sulphonic acids, such as, for example, acetic acid, trifluoroacetic acid, trichloroacetic acid, methanesulphonic acid, ethanesulphonic acid, benzenesulphonic acid or toluenesulphonic acid.

The reduction of the acid amides is carried out either by means of hydrogen in water or inert organic solvents in alcohols, ethers or halogenated hydrocarbons or their mixtures, using catalysts such as Raney nickel, palladium, palladium on animal charcoal or platinum, or else using hydrides in inert solvents, if appropriate in the presence of a catalyst, or using boranes, diboranes or their complex compounds.

The reactions are preferably carried out using hydrides, such as complex borohydrides or aluminium hydrides. Sodium borohydride, lithium aluminum hydride, sodium cyanoborohydride or hydroboric acid are particularly preferably employed in this connection.

The compounds of the general formula (XIX) are known per se or can be prepared by customary methods (J. Med. Chem. 1972, 15, 8650, J. Gen. Chem. (USSR) 36, 3856 (1960).

The compounds of the formula (XXII) are known or can be prepared by customary methods (J. Med. Chem., 1972, 15, No. 8, Publs. Soc. Chim. Tr. 1958, 325, J. Am. Chem. Soc. (9, 2341, 1947).

The halogen compounds of the general formulae (III) and (XI) are known or can be prepared by known methods [Beilstein's Handbuch der organischen Chemie (Beilstein's Handbook of Organic Chemistry) 2, 197,201, 250, 278; 3, 9, 10; 21, 461, 462, 463].

Halogen compounds which can be used, for example, according to the invention are: chloroacetonitrile, 2-chloropropionitrile, 3-chlorobutyronitrile, 3-bromopropylphthalimide, 3-chloropropylphthalimide, 2-bromoethylphthalimide, 4-bromobutylphthalimide, 4-chlorobutylphthalimide, N,N-diethylchloroacetamide N,N-dimethylchloroacetamide, methyl chloroacetate, ethyl chloroacetate, ethyl bromoacetate, methyl bromoacetate, 2-δ-bromobutyl-1,2-benzoisothiazole-(2H)-one-1,1-dioxide or 2-γ-bromopropyl-1,2-benzoisothiazole-3(2H)-one-1,1-dioxide.

The aldehydes of the general formulae (IV) and (XII) employed as starting materials are known or can be prepared by known methods [Beilstein's Handbuch der organischen Chemie (Beilstein's Handbook of Organic Chemistry) 1, 594, 629, 662].

Aldehydes which can be used, for example, according to the invention are: acetaldehyde, propionaldehyde, butyraldehyde or benzaldehyde.

The compounds according to the invention can be used as active compounds in medicaments.

The substances according to the invention have a particularly high affinity for cerebral 5-hydroxytryptamine receptors of the 5-$HT_1$ type.

They have agonistic, partially agonistic or antagonistic effects on the serotonin receptor. In comparison to the structurally related known compounds, they surprisingly exhibit a greater therapeutic breadth.

The high-affinity ligands for the serotonin-1 receptor described in the present invention thus represent active compounds for controlling diseases which are characterized by disturbances of the serotoninergic system, in particular with involvement of receptors which have a high affinity for 5-hydroxytryptamine (5-$HT_1$ type). They are therefore suitable for the treatment of disorders of the central nervous system such as anxiety, tension and depression states, sexual dysfunctions caused by the central nervous system and disturbances in sleep and the absorption of food. Furthermore, they are suitable for eliminating cognitive deficiencies, for improving powers of learning and memory and for treating Alzheimer's disease.

Furthermore, these active compounds are also suitable for the modulation of the cardiovascular system. They also intervene in the regulation of the cerebral circulation and thus represent effective agents for controlling migraine.

They are also suitable for the prophylaxis and control of the effects of occurrences of cerebral infarct (Apoplexia cerebri) such as stroke or cerebral ischaemia. The compounds according to the invention can also be employed for the control of pain states. They are also suitable for the control of disorders of the intestinal tract which are characterized by disturbances of the serotoninergic system and also by disturbances of the carbohydrate metabolism.

The new active compounds may be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration from about 0.5 to 90% by weight of the total mixture, i.e. in amounts which are sufficient in order to achieve the dosage range indicated.

The formulations are prepared, for example, by extending the active compounds using solvents and/or excipients, if appropriate using emulsifiers and/or dispersants, where, for example, in the case of the use of water as a diluent if appropriate organic solvents may be used as auxiliary solvents.

Auxiliaries which may be mentioned, for example, are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example kaolins, aluminas, talc, chalk), ground synthetic minerals (for example highly disperse silica, silicates), sugar (for example sucrose, lactose and dextrose), emulsifiers (for example polyoxyethylene fatty acid esters, polyoxyethylene fatty alcohol ethers), dispersants (for example lignin-sulphite waste liquors, methylcellulose, starch and polyvinyl-pyrrolidone) and lubricants (for example magnesium stearate, talc, stearic acid and sodium sulphate).

Administration takes place in a customary manner, preferably orally or parenterally, in particular perlingually or intravenously. In the case of oral administration, tablets may, of course, also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc may additionally be used for tabletting. In the case of aqueous suspensions, various flavor enhancers or colorants may be added to the active compounds in addition to the abovementioned auxiliaries.

In the case of parenteral administration, solutions of the active compounds may be employed using suitable liquid excipients.

In general, it has proved advantageous on intravenous administration to administer amounts of about 0.001 to 1 mg/kg, preferably about 0.01 to 0.5 mg/kg, of body weight to obtain effective results, and on oral administration the dosage is about 0.01 to 20 mg/kg, preferably 0.1 to 10 mg/kg, of body weight.

In spite of this, it may sometimes be necessary to depart from the amounts mentioned, depending on the body weight or the type of application route, on individual behaviour towards the medicament, the manner of its formulation and the point in time or interval at which administration takes place. Thus, in some cases it may be sufficient to manage with less than the minimum amount previously mentioned, whereas in other cases the upper limit mentioned must be exceeded. In the case of the administration of larger amounts, it may be advisable to divide these into a number of individual doses over the day.

PREPARATION EXAMPLES

The $R_f$ values were in each case determined—unless stated otherwise—by thin layer chromatography on silica gel (aluminum foil, silica gel 60 F 254, E. Merck). Visualization of the substance streaks was carried out by examining under UV light and/or by spraying with 1% strength potassium permanganate solution.

Flash chromatography was carried out on silica gel 60, 0.040–0,064 mm, E. Merck (see Still et al., J. Org. Chem. 43, 2923, 1978; for relatively simple separation problems see Aldrichimica Acta 18, 25, 1985). Elution using solvent gradients means: beginning with the pure, non-polar solvent mixture component, the polar eluent component is admixed to an increasing extent until the desired product is eluted (TLC checking).

In all products, the solvent was finally distilled off at 0.1 torr. Salts were stored at this pressure overnight over potassium hydroxide and/or phosphorus pentoxide.

Starting Compounds and Preparation Examples

EXAMPLE 1

2-Aminomethyl-5-methoxy-chroman

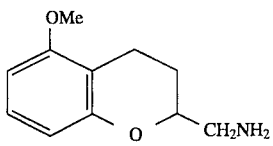

0.85 g (4.1 mmol) of 2-carboxamido-5-methoxychroman in 5 ml of THF was added dropwise to a boiling suspension of 0.30 g (8.2 mmol) of lithium aluminum hydride in 5 ml of THF. After heating to reflux for 3 h, the mixture was cooled and 0.3 ml of water and 0.5 ml of 20% sodium hydroxide solution were successively added. Filtration over kieselguhr and concentration gave 0.62 g of crude product which was purified by flash chromatography (toluene-ethyl acetate, then ethanol gradients). Yield: 0.52 g (66%) $R_f$: (toluene/methanol 4:1)=0.16 IR (CHCl$_3$): 3389, 3009, 2947, 1607, 1593, 1470.

EXAMPLE 2

2-(N-Propyl) aminomethyl-chroman

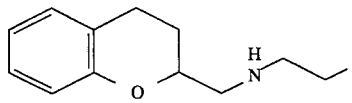

The compound was prepared analogously to the directions of Example 1. IR (CHCl$_3$): 3320 (broad), 3010, 2965, 2879, 1607, 1584, 1490, 1457, 1235.

EXAMPLE 3

2-(N-Propyl)aminomethyl-5-methoxy-chroman

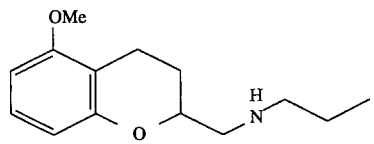

The compound was prepared analogously to the directions of Example 1. $^1$H-NMR (CDCl$_3$): 0.85 (t; 3H), 1.55 (quint.; 3H), 1.7 (m; 1H), 2.0 (m; 1H), 2.5–3.0 (m; 6H), 3.7 (s; 3H), 4.1 (m, 1H), 6.4 (d; 1H), 6.5 (d; 1H), 7.0 (t, 1H).

EXAMPLE 4

2-Aminomethyl-benzo(h)chroman hydrochloride

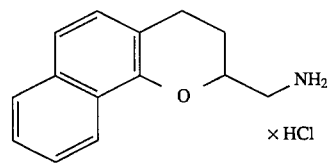

The compound was prepared analogously to Example 24 from 2-carboxamido-benzo(h)chroman.

EXAMPLE 5

1-Methoxy-5,6-dihydro-7-nitromethyl-naphthalene

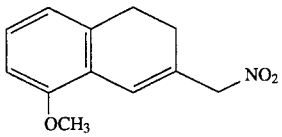

44.1 g of 8-methoxy-2-tetralone (0.25 mol) are stirred at 70° C. under argon for 3 h in 402 ml of nitromethane (7.50 mol) and 2.5 ml of ethylenediamine. After the mixture has cooled to room temperature, a yellow crystallisate is filtered off with suction. The nitromethane is distilled off from the solution in vacuo. The residue is dissolved in 500 ml of toluene. The solvent is again distilled off in vacuo in order to remove nitromethane residues. The residue is then dissolved in 200 ml of toluene again. An insoluble component is filtered off and the solution is concentrated to 50 ml. The concentrated solution is then chromatographed on 500 g of silica gel using toluene. After concentrating the main fraction, the final product is obtained as a yellow oil. Yield: 40.4 g=73% of theory $R_f$=0.45

EXAMPLE 6

2-Aminomethyl-8-methoxytetralin

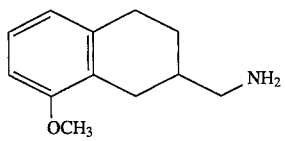

14.9 g of the compound from Example 5 (68 mmol) are hydrogenated in 300 ml of methanol using elemental hydrogen. 3.4 g of palladium/active charcoal are employed as a catalyst. The temperature is limited to 25°–30° C. by slight cooling.

The catalyst is then filtered off with suction and the reaction solution is substantially concentrated in vacuo. 300 ml of toluene are then added and distilled off again in vacuo in order to remove methanol residues. The residue is again dissolved in 300 ml of toluene, and the solution is washed with 5% strength potassium carbonate solution and water. The organic phase is dried over sodium sulphate. The solvent is then again distilled off in vacuo.

The crude product is dissolved in 25 ml of toluene and the solution is applied to 60 g of silica gel 60 (Merck). The silica gel is first washed with toluene and the final product is then eluted using methanol/triethylamine 95:5. A pale yellow oil is obtained after concentrating the methanolic solution. Yield: 9.5 g=73% of theory $R_f$: 0.28 (silica gel; methanol/triethylamine 95:5)

EXAMPLE 7

2-(N-Benzyl)-aminomethyl-8-methoxytetralin

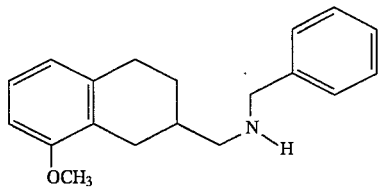

13.4 g of 2-aminomethyl-8-methoxytetralin (70 mmol) are dissolved in 420 ml of methanol. 3.0 ml of acetic acid (52.5 mmol) are then added dropwise. A further 5.3 g of sodium cyanoborohydride (84 mmol) are added after 5 minutes. The reaction solution is warmed to 60° C. and a solution of 7.4 g of benzaldehyde (70 mmol) in 74 ml of methanol is then added dropwise in the course of 30 minutes. The mixture is then boiled under reflux for 3 h.

After cooling, the solvent is distilled off in vacuo and the residue is dissolved in 420 ml of dichloromethane and 210 ml of water. The organic phase is again washed with water and dried over sodium sulphate. The solvent is again distilled off in vacuo and the residue is stirred with 700 ml of diethyl ether and 140 ml of 5N sodium hydroxide solution. The organic phase is washed with water until neutral and dried over sodium sulphate. The solvent is distilled off in vacuo.

The residue is chromatographed on 200 g of silica gel 60 (Merck). Diisopropyl ether is used as the eluent. The final product in this case is obtained as a colorless viscous oil. Yield: 11.7 g=59% of theory $R_f$=0.25 (silica gel; toluene/methanol 95: 5)

EXAMPLE 8

2-[N-Benzyl-N-2'-cyanoethyl]-aminomethyl-8-methoxytetralin

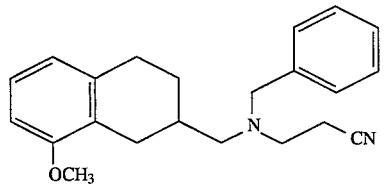

11.7 g of the compound from Example 7 (41.6 mmol) and 0.15 g of copper acetate in 13.7 ml of acrylonitrile (208 mmol) were boiled under reflux for 2 h under argon. The mixture was then diluted using 7 ml of acrylonitrile. After the mixture had slowly cooled to room temperature, it was cooled to 10° C. after 2 h. The crystallisate was filtered off with suction and dried at 40° C. in vacuo. Yield: 10.6 g=76% of theory $R_f$=0.77 (silica gel; toluene/methanol 95: 5) M.p.:= 111°–112° C.

EXAMPLE 9

2-[N-Benzyl-N-3'-aminopropyl]-aminomethyl-8-methoxytetralin

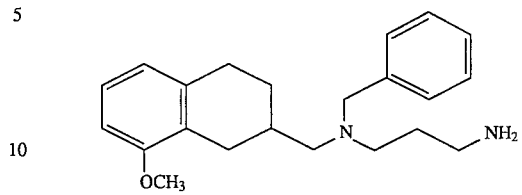

4.8 g of lithium aluminum hydride (125.6 mmol) are suspended under argon in 315 ml of absolute diethyl ether. 10.5 g of the compound from Example 8 (31.4 mmol) are then introduced in portions in the course of 20 minutes. The temperature is in this case limited to 20°–25° C. by slight cooling. The mixture is then stirred at room temperature for a further 3 h.

A mixture of 260 ml of tetrahydrofuran and 15 ml of water is then added dropwise. The mixture is stirred for 30 minutes and the precipitate is then filtered off with suction. The solution is concentrated to 250 ml and stirred into 2.5 l of water. The mixture is extracted using toluene and the organic phase is washed until neutral and dried over sodium sulphate. After the solvent has been distilled off in vacuo, the final product remains as a pale yellow oil. Yield: 10.1 g=95% of theory $R_f$=0.32 (silica gel; methanol/toluene 95:5)

EXAMPLE 10 AND EXAMPLE 11

2-{N-[4-(1,1-Dioxido-3-oxo-2,3-dihydro-benzisothiazol-2yl)butyl] aminomethyl}-8-methoxytetralin

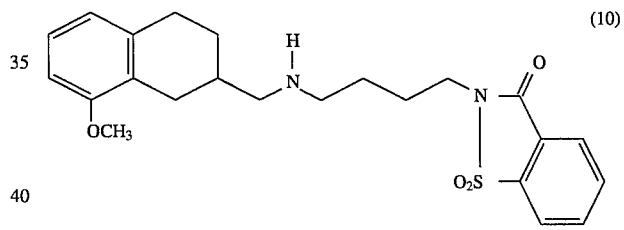

(10)

2-{N-Di[4-(1,1-dioxido-3-oxo-2,3-dihydro-benzisothiazol-2-yl)butyl]aminomethyl}-8 -methoxytetralin

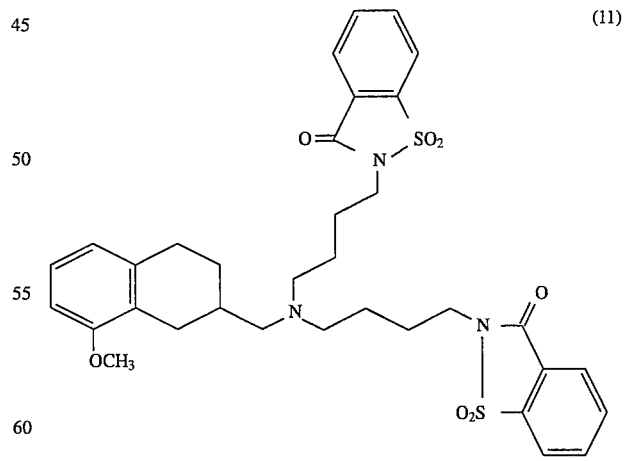

(11)

0.95 g of 2-aminomethyl-8-methoxytetralin (5 mmol), 0.70 ml of triethylamine (5mmol) and 1.59 g of 2-(4-bromobutyl)-1,2-benzisothiazol-3(2H)-one 1,1-dioxide (5 mmol) are stirred at 40° C. for 24 h in 19 ml of dimethylformamide. The reaction solution is then stirred into a mixture of 190 ml of 5% strength sodium chloride solution, 60 ml of toluene and 5 ml of 1N hydrochloric acid. After the organic phase has been separated off, the aqueous phase containing the final product precipitated as the resinous hydrochloride is stirred with 60 ml of toluene and 7 ml of triethylamine (50 mmol). The organic phase is separated off again, washed until neutral with water and dried over sodium sulphate. The solvent is distilled off in vacuo. The residue is chromatographed on silica gel 60 (Merck). Toluene/methanol 85:15 is in this case used as the eluent. The main fractions contain the two final products as yellow, viscous oils.

Both bases can be precipitated as the hydrochloride from toluene solution using ethereal hydrogen chloride solution.

EXAMPLE 10

Yield: 0.59 g=28% of theory $R_f$: 0.30 silica gel; (toluene/methanol 85:15)

EXAMPLE 11

Yield: 0.50 g=15% of theory $R_f$: 0.73 silica gel; (toluene/methanol 85:15)

EXAMPLE 12

2-{N-Methyl-N[4-(1,1-dioxido-3-oxo-2,3-dihydro-benzisothiazol-2-yl) butyl]aminomethyl}-8-methoxytetralin

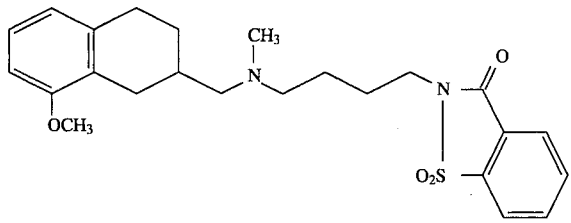

2.9 g of 2-aminomethyl-8-methoxytetralin (15 mmol), 2.1 ml of triethylamine (15 mmol) and 4.8 g of 2-(4-bromobutyl)-1,2-benzisothiazol-3(2H)-one 1,1-dioxide (15 mmol) are stirred at 40° C. for 50 h in 58 ml of dimethylformamide. A solution of 1.4 g of methyl iodide (10 mmol) and 3.2 ml of dimethyl formamide is then added dropwise and the mixture is stirred at 40° C. for a further 18 h.

The reaction solution is then stirred into a mixture of 600 ml of water, 3.8 g of potassium carbonate (27.5 mmol) and 300 ml of toluene. The organic phase is washed with water until neutral and dried over sodium sulphate. The solvent is distilled off in vacuo.

The residue is dissolved in a diisopropyl ether-toluene mixture (80:20) and prepurified by filtration through 20 g of silica gel. The final product is isolated from the residue obtained by distilling off the solvent by means of column chromatography on silica gel 60 (Merck). Ethyl acetate is in this case used as the eluent.

The hydrochloride can be precipitated from the toluene solution as a solid by using ethereal hydrogen chloride solution.

Yield: 0.85=12.9% of theory $R_f$=0.25 (silica gel; ethyl acetate or toluene/methanol 95:5)

EXAMPLE 13 AND EXAMPLE 14

2-{N-[4-(1,1-Dioxido-2H-naphth[1,8-cd]-isothiazol-2-yl)butyl]aminomethyl}-8-methoxytetralin

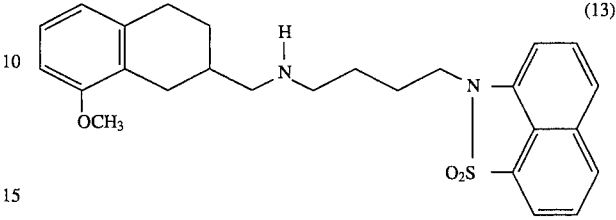

2-{N-Di[4-(1,1-dioxido-2H-naphth[1,8-cd]isothiazol-2-yl)butyl]aminomethyl}-8-methoxytetralin

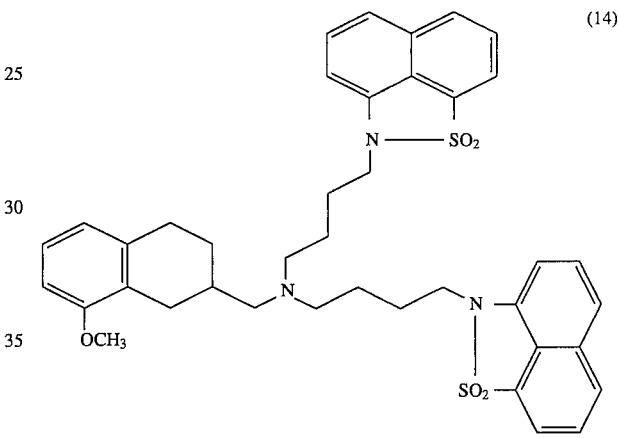

1.6 g of 2-amino-8-methoxytetralin (8.4 mmol), 1.16 ml of triethylamine (8.4 mmol) and 1.59 g of 2-(4-bromobutyl)-2H-naphth[1,8-cd]isothiazole 1,1-dioxide are stirred for 48 h at 40° C. in 32 ml of dimethylformamide. The reaction solution is then stirred into a mixture of 320 ml of 5% strength sodium chloride solution, 100 ml of toluene, 8.4 ml of 1N hydrochloric acid and kieselguhr. The kieselguhr containing the hydrochloride of the final product attached thereto is filtered off with suction—and introduced into a mixture of 300 ml of water and 100 ml of toluene. The final product is transferred to the organic phase by dropwise addition of 9 ml of 1N sodium hydroxide solution.

After filtration, the organic phase is separated off, washed with water until neutral and dried over sodium sulphate. After the solvent has been distilled off in vacuo, the residue is separated into the two final products by column chromatography on silica gel 60 (Merck). Ethyl acetate is in this case used as the eluent.

Both bases can be precipitated as the hydrochloride from ethereal solution using ethereal hydrogen chloride solution.

Example 13

Yield: 1.51 g=39.8% of theory $R_f$=0.28

Example 14

Yield: 0.63 g=10.6% of theory $R_f$=0.60

EXAMPLE 15

2-{N-[4-(1,1-Dioxido-3-oxo-4-phenyl-3,4-dihydro-2H-1,2,4-benzothiadiazin-2-yl)butyl]aminomethyl}-8-methoxytetralin

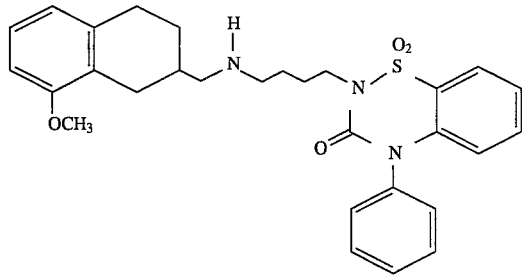

0.95 g of 2-aminomethyl-8-methoxytetralin (5 mmol), 0.70 ml of triethylamine (5 mmol) and 2.05 g of 2-(4-bromobutyl)-3-oxo-4-phenyl-3,4-dihydro-2H-1,2,4-benzothiadiazine 1,1-dioxide are stirred for 24 h at 40° C. in 19 ml of dimethylformamide. The reaction solution is then stirred into a mixture of 190 ml of 5% strength sodium chloride solution, 60 ml of toluene and 5 ml of 1N hydrochloric acid. After the organic phase has been separated off, the aqueous phase containing the final product precipitated as the resinous hydrochloride is stirred with 60 ml of toluene and 7 ml of triethylamine (50 mmol). The organic phase is separated off again, washed until neutral with water and dried over sodium sulphate. The solvent is distilled off in vacuo. The residue is chromatographed on silica gel 60 (Merck). Toluene/methanol 85:15 is used as the eluent in this case.

The hydrochloride can be precipitated as a solid from the toluene solution using ethereal hydrogen chloride solution.

Yield: 0.83 g=31.9% of theory $R_f$=0.28 (silica gel; toluene/methanol 85:15),

M.p.: 148° C.

EXAMPLE 16

2-{N-Benzyl-N-[3-(4-fluorophenylsulphonylamido)-propyl]aminomethyl}- 8-methoxytetralin

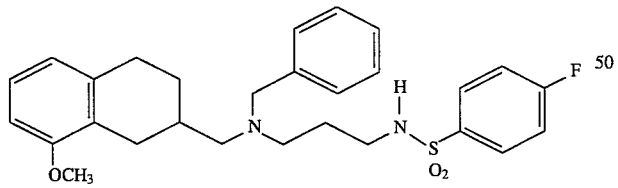

0.95 g (2.8 mmol) of the compound from Example 9 is dissolved in 19 ml of dichloromethane. After addition of 0.39 g (2.8 mmol) of finely ground potassium carbonate, a solution of 0.60 g of 4-fluorobenzenesulphonyl chloride and 9.5 ml of dichloromethane is added dropwise at 15°–20° C. The reaction solution is then stirred at room temperature for a further 18 h.

15 ml of water are then added. The organic phase is washed until neutral with water, dried over sodium sulphate and concentrated in vacuo. The residue is dissolved in 50 ml of diisopropyl ether, and the solution is filtered. The solution is then again concentrated to about 10 ml and chromatographed on 25 g of silica gel. Diisopropyl ether is used as the eluent. The final product is obtained as a pale brown viscous oil.

Yield: 1.08 g=78% of theory $R_f$=0.58 (silica gel; toluene/methanol 95:5)

$R_f$=0.23 (silica gel; diisopropyl ether)

EXAMPLE 17

2-{N-[3-(4-Fluorophenylsulphonylamido)propyl]-aminomethyl}- 8-methoxytetralin

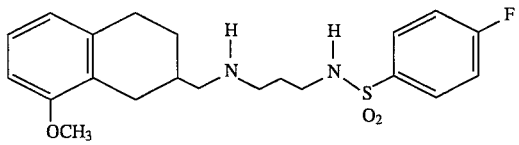

1.0 g of the compound from Example 16 (2 mmol) is hydrogenated in 50 ml of methanol and 2.4 ml of methanolic hydrogen chloride solution (0.9 mmol/ml) using elemental hydrogen. 0.1 g of palladium/activated charcoal is employed as the catalyst.

The catalyst is then filtered off and the solution is concentrated to 10 ml in vacuo. The solution is then stirred into a mixture of 100 ml of water, 50 ml of dichloromethane and 2.5 ml of 1N sodium hydroxide solution. The organic phase is washed until neutral with water, dried over sodium sulphate and concentrated in vacuo.

The residue is applied to 20 g of silica gel, and starting material residues are first eluted using diisopropyl ether, then the final product using methanol. After the methanol has been distilled off, the residue becomes crystalline on Stirring with diisopropyl ether. The white crystallisate is filtered off with suction and dried at 50° C. in vacuo.

Yield: 0.47 g=58% of theory $R_f$=0.25 (silica gel; toluene/methanol 85:15)

M.p.: 111°/112°–114° C.

EXAMPLE 18

2-{N-Benzyl-N-[3-(ethoxycarbonylamido)propyl]-aminomethyl}- 8-methoxytetralin

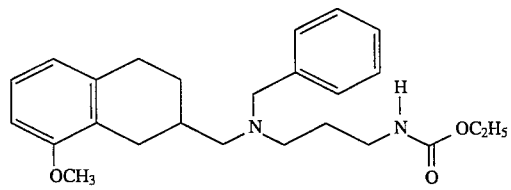

The compound is obtained from 1.80 g of the compound from Example 9 (5.3 mmol) and 0.55 ml of ethyl chloroformate (5.8 mmol) as a viscous oil analogously to the working directions for the compound 16.

Yield: 2.00 g=92% of theory $R_f$=0.50 (silica gel; toluene/methanol 95:5)

$R_f$=0.30 (silica gel; diisopropyl ether)

EXAMPLE 19

2-{N-[3-(Ethoxycarbonylamido)propyl]aminomethyl}-8-methoxytetralin

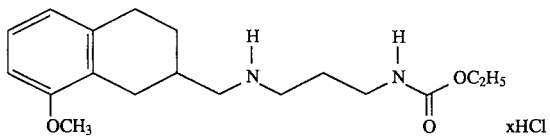

The compound is obtained as a viscous oil after hydrogenation from 1.80 g of the compound from Example 18, 90 ml of methanol, 7.3 ml of methanolic hydrogen chloride solution and 0.22 g of palladium/activated carbon analogously to the working directions for compound 17.

The base is dissolved in ether and an insoluble component was filtered off. The hydrochloride is precipitated from the solution using ethereal hydrogen chloride solution. The white solid is filtered off with suction and dried in vacuo at 40° C.

Yield: 0.60 g=38% of theory $R_f$=0.40 (silica gel; toluene/methanol 70:30)

$R_f$=0.20 (base)

M.p.: 188°/191°–193° C.

EXAMPLE 20

2-{N-[4-(1,1-Dioxido-3-oxo-2,3-dihydro-benzisothiazol-2-yl)butyl-N-propyl] aminomethyl}-chroman

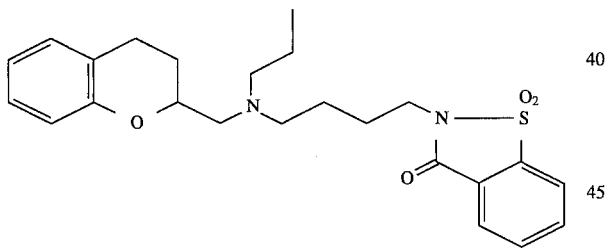

A mixture of 4.90 g (24 mmol) of 3,4-dihydro-2-(N-propyl)aminomethyl-2 H-chromene, 8.60 g (27 mmol) of 2-(4-bromobutyl)-1,2-benzisothiazol-3(2H)-one 1,1-dioxide, 6.6 g (48 mmol) of powdered potassium carbonate and 0.1 g of sodium iodide in 100 ml of anhydrous dimethylformamide was stirred at 60°–70° C. for 12 h.

After filtering and concentrating at about 2 torr, the mixture was purified by flash chromatography (toluene/ethyl acetate gradient; silica gel). In this manner, 4.5 g (44%) of product were obtained as a viscous oil.

$R_f$: (toluene/methanol 4:1) 0.47

IR (CHCl$_3$): 3011, 2958, 2874, 1733, 1598, 1584, 1489.

The hydrochoride was obtained as a colorless, amorphous solid by treatment with ethereal hydrochloric acid in ether.

$^1$H-NMR (CD$_3$OD): 1.0 (t; 3H), 1.6–2.2 (m; 8H), 2.7–3.0 (m; 2H), 5.2–3.6 (m; solvent signal underneath, CHD$_2$OD), 3.9 (m; 2H), 4.5 (m; 1H), 6.75–7.1 (m; 4H), 7.8–8.2 (m; 4H), 7.9 (s; —OH, —NH—)

EXAMPLE 21

3-{N-[4-(1,1-Dioxido-3-oxo-2,3-dihydro-benzisothiazol-2-yl)butyl] amiomethyl}-chroman

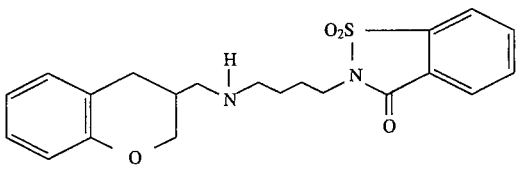

Preparation is carried out from 3-aminomethyl-chroman analogously to the directions of Example 20.

$R_f$: (toluene/methanol 4:1): 0.33.

The hydrochloride is obtained by precipitation with ethereal hydrochloric acid.

Amorphous, hygroscopic solid.

$^1$H-NMR (hydrochloride; CD$_3$OD): 1.8–2.0 (m; NH), 2.4 (m; 1H), 2.65 ("dd"; 1H) 2.9–3.2 (m; 5H), 3.75 (t; 2H), 4.0 (m; 1H), 4.25 (m; 1H), 6.7–7.1 (m; 4H), 7.9–8.1 (m; 4H)

EXAMPLE 22

3-{N,N-Di[1,1-dioxido-3-oxo-2,3-dihydro-benzisothiazol- 2-yl)butyl]aminomethyl}-chroman

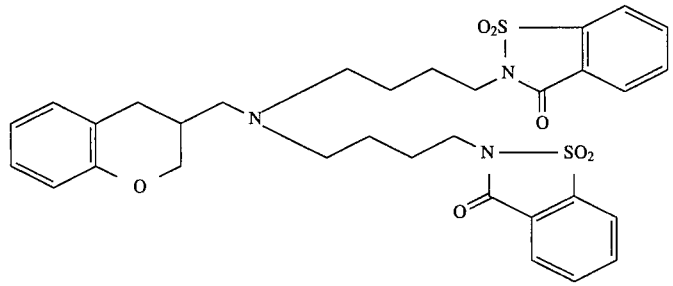

In addition to Example 21, the compound 22 is formed in the reaction of 3-aminomethyl-chroman with 4-bromobutyl-saccharin.

$R_f$: (toluene/ethyl acetate 1:1): 0.58

The hydrochloride is obtained as an amorphous solid by treating with ethereal hydrochloric acid:

$^1$H-NMR (hydrochloride, CD$_3$OD): 1.8–2.0 (m; 8H), 2.5–2.8 (m; 2H), 2.9–3.4 (m; contains solvent signals), 3.75 (m; 4H), 4.0 (m; 1H), 4.25 (m; 1H), 6.7–7.1 (m; 4H), 7.9–8.1 (m; 8H) and also signals from about 8% diethyl ether.

EXAMPLE 23

2-[N-2-(4-Fluorophenylsulphonamido)ethyl]-carboxamido-2H-chroman

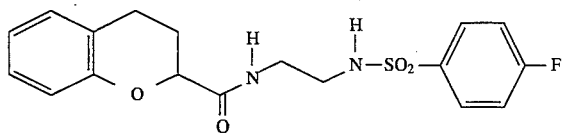

The reaction of 2-chromancarbonyl chloride and 2-(4-fluorophenylsulphonamido)ethylamine in the presence of sodium hydrogen carbonate in ether/dioxane gives compound 23.

R$_f$: (toluene/ethyl acetate 1:1): 0.35

EXAMPLE 24

2-[N-(4-Fluorophenylsulphonylamido)ethyl]-aminomethyl-chroman Hydrochloride

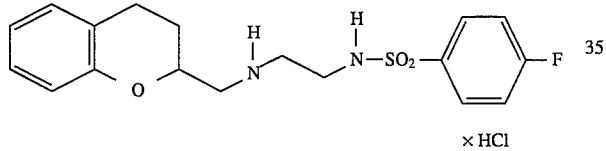

A solution of 4.50 g (11.9 mmol) of the compound from Example 23 in 100 ml of absolute THF was added at 0° C. to 16.6 ml (16.6 mmol) of a 1M solution of BH$_3$ in THF.

50 ml of THF were then added dropwise. After stirring for 2 hours at room temperature the mixture was cooled to 0° and 2 ml of concentrated hydrochloric acid were added.

The precipitate was filtered off with suction after 30 minutes and washed with THF and n-hexane. In this manner, 3.35 g (70%) of product were obtained as colorless crystals.

Melting point: 212°–214° C.

MS: 364, 231, 176 (100%), 95

$^1$H-NMR (CD$_3$OD): 1.75 (m; 1H), 2.1 (m; 1H), 2.7–3.0 (m; 2H), 3.1–3.5 (m; contains solvent signal). 4.4 (m; 1H), 6.8 (m; 2H), 7.1 (m; 2H), 7.2–7.4 (m; 2H), 8.0 (m; 2H).

EXAMPLE 25

2-Aminomethyl-7,8,9,10-tetrahydro-benzo(h)-chroman Hydrochloride

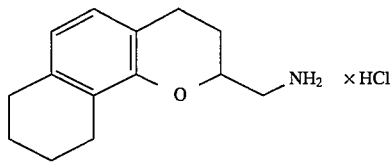

The preparation is carried out from the corresponding carboxamide using borane-THF complexes analogously to the working directions of Example 24.

$^1$H-NMR (CD$_3$OD): 1.4–1.9 (m; 5H), 2.0–2.1 (m; 1H), 2.6–3.0 (m; 6H) , 3.1–3.4 (m; several H; also CD$_2$HOD), 4.2–4.3 (m; 1H), 4.9 (s; H$_2$O, — NH$_2$), 6.6 (d; 1H), 6.8 (d; 1H).

The free base was obtained using sodium hydrogen carbonate/ethyl acetate extraction.

Rf: (dichloromethane/methanol 10:1): 0.27

EXAMPLE 26

2-{N-[4-(1,1-Dioxido-3-oxo-2,4-dihydro-benzisothiazol-2-yl)-butyl]aminomethyl}-7,8,9,10-tetrahydro-benzo(H)chroman

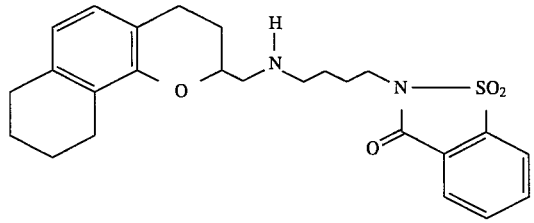

The compound from Example 25 was prepared analogously according to the working procedure of Example 20.

MS: 454, 424, 267, 200

R$_f$: (CH$_2$Cl$_2$/CH$_3$OH 10:1), 0.58

The corresponding hydrochloride is amorphous.

$^1$H-NMR (CD$_3$OD): 1.6–2.1 (m; 10H), 2.5–3.0 (m; 5H), 3.1–3.4 (m; several H, underneath CD$_2$HOD), 3.9 (t; 2H), 4.3 (m; 1H), 4.9 (s; H$_2$O, NH), 6.6 (d; 1H), 6.75 (d; 1H), 7.9–8.1 (m; 4H).

EXAMPLE 27

2-(N,N-{Di[4-(1,1-dioxido-3-oxo-2,3-dihydro-benzisothiazol- 2-yl)butyl]aminomethyl)-7,8,9,10-tetrahydro-benzo(h)chroman

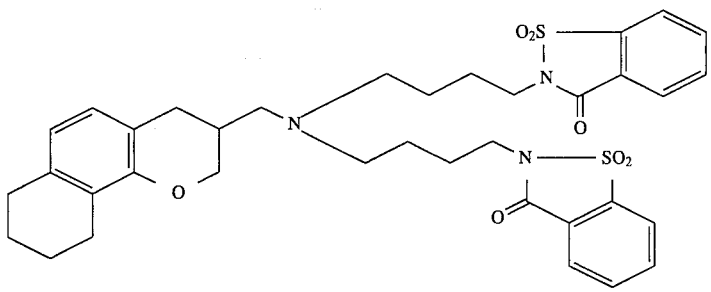

The compound is formed in the preparation of Example 26.

R$_f$: (CH$_2$Cl$_2$/CH$_3$OH 10:1) 0.86

The amorphous hydrochloride of the compound was precipitated using ethereal hydrochloric acid in ether.

$^1$H-NMR (CD$_3$OD): 1.4–2.1 (m; 14H), 2.5–3.0 (m; 7H), 3.2–3.6 (m; several H; underneath CD$_2$HOD), 3.9 (m; 4H), 4.5 (m; 1H), 4.9 (s; H$_2$O, NH), 6.5 (d; 1H), 6.75 (d; 1H), 7.9–8.1 (m; 8H).

EXAMPLE 28

2-{N-[4-(1,1-Dioxido-3-oxo-2,3-dihydro-benziso-thiazol-2-yl)butyl] aminomethyl}chroman

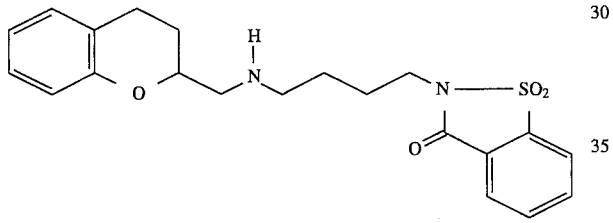

The compound is prepared from 2-aminomethyl-3,4-dihydro- 2H-chromene analogously to the working directions of Example 20.

The corresponding hydrochloride has a melting point of 188° C.–195° C.

R$_f$: (toluene/ethyl acetate 1:1)=0.37

EXAMPLE 29

2-{N-[4-(1,1-Dioxido-3-oxo-2,3-dihydro-benziso-thiazol-2-yl)butyl] aminomethyl}-8-methoxy-chroman

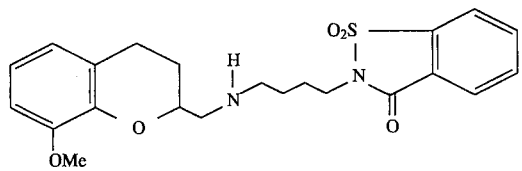

The compound is prepared from 2-aminomethyl-3,4-dihydro- 8-methoxy-2H-chromene analogously to the working directions of Example 20.

R$_f$: (toluene/methanol 4:1): 0.33

The corresponding hydrochloride has a melting point of 173°–178° C.

EXAMPLE 30

2-{N-[4-(1,1-Dioxido-3-oxo-2,3-dihydro-benziso-thiazol-2-yl)butyl] aminomethyl}-5-methoxy-chroman

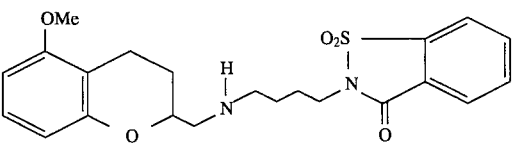

The compound is prepared from 2-aminomethyl-3,4-dihydro- 5-methoxy-2H-chromene analogously to the working directions of Example 20.

R$_f$: (toluene/methanol 4:1) 0.3

The hydrochloride has a melting point of 253°–257° C.

EXAMPLE 31

2-{N-[4-(1,1-Dioxido-3-oxo-2,3-dihydro-benziso-thiazol-2-yl)butyl]-N-propyl] aminomethyl}-5-methoxy-chroman

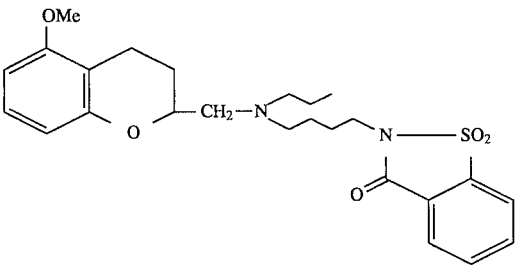

The compound is prepared from 3,4-dihydro-2-(n-propyl)aminomethyl- 5-methoxy-2H-chromene analogously to the working directions of Example 20.

R$_f$: (toluene/methanol 4:1), 0.33

MS: 472, 309, 196

The corresponding hydrochloride exhibits the following shifts:

$^1$H-NMR (CD$_3$OD): 1.0 (t; 3H), 1.6–2.2 (m; 8H), 2.5–2.9 (m; 2H), 3.1–3.5 (m; contains signal from CD$_2$HOD), 3.7. (s; 3H), 3.9 (t; 2H), 4.4 (m; 1H), 4.9 (s; H$_2$O, —NH), 6.5 (m; 2H), 7.0 (m; 1H), 7.8–8.1 (m; 4H)

EXAMPLE 32

2-{N-[4(1,1-Dioxido-3-oxo-2,3-dihydro-benzisothiazol-2-yl)butyl] aminomethyl}benzo(h)chroman

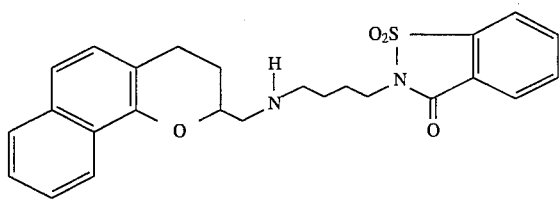

The compound is prepared from 2-aminomethyl-3,4-dihydro- 2H-benzo(h)chromene hydrochloride analogously to the working directions of Example 20.

M.p.: 97°–102° C.

EXAMPLE 33

2-{N-[4-(1,1-Dioxido-2H-naphth[1,8-cd]isothiazol-2-yl)butyl] aminomethyl}-chroman

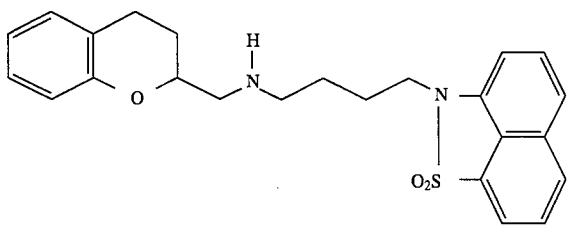

The compound is prepared from 2-aminomethyl-3,4-dihydro- 2H-chromene and 2-(4-bromobutyl)-2H-naphth[1,8cd] isothiazole 1,1-dioxide (available from 2H-naphth[1,8-cd]isothiazole 1,1-dioxide and 1,4-dibromobutane using a base) according to the working directions of Example 20.

$R_f$: (toluene/ethyl acetate 1:1)=0.41

The corresponding hydrochloride is amorphous.

$^1$H-NMR (CD$_3$OD): 1.7 (m; 1H), 2.0 (m; 5H), 2.6–2.9 (m; 2H), 3.2–3.5 (m; underneath signals from the solvent), 3.9 (m; 2H), 4.5 (m; 1H), 6.65 (dd; 1H), 6.75 (ddd; 1H), 6.9–7.1 (m; 2H), 7.5–7.6 (m; 2H), 7.8 (dd; 1H), 8.05 (d; 1H), 8.2 (d; 1H).

EXAMPLE 34

2-{N-Benzyl-N-[3-(N-benzyl-4-fluorophenyl-sulphonamido)propyl]aminomethyl}-8-methoxytetralin

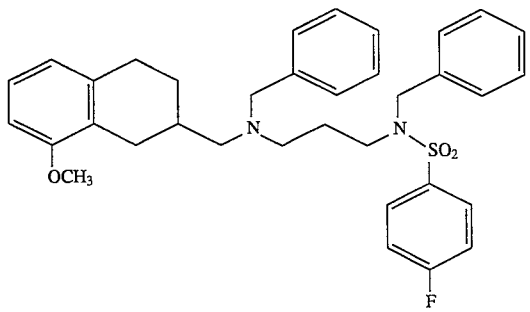

79 mg of sodium hydride (3.3 mmol) are suspended under argon in 15 ml of dry dimethylformamide. A solution of 1.49 g of the compound from Example 16 (3 mmol) in 15 ml of dry dimethylformamide is then added dropwise at 20°–25° C. in the course of 30 minutes. The mixture is then warmed to 30° C. for a further 1 h. A solution of 0.56 g of benzyl bromide (3 mmol) in 15 ml of dry dimethylformamide is then added dropwise in the course of 15 minutes. The mixture is stirred at room temperature for a further 18 h in order to complete the reaction.

For working up, the mixture is stirred into a mixture of 450 ml of 5% strength sodium chloride solution and 150 ml of toluene. The organic phase is washed with water until neutral and dried over sodium sulphate, and the solvent is distilled off.

The crude product is chromatographed on 90 g of silica gel 60 using diisopropyl ether. A colorless resin is obtained.

Yield: 1.26 g=76% of theory $R_f$=0.52 (silica gel, diisopropyl ether)

EXAMPLE 35

2-{N-[3-(N-Benzyl-4-fluorophenylsulphonamido)-propyl] aminomethyl}-8-methoxytetralin

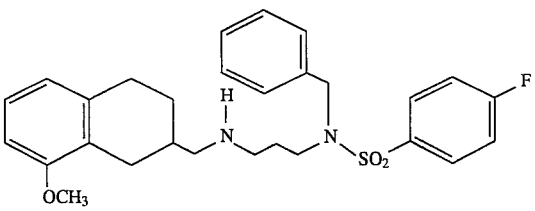

The compound is obtained as a viscous oil after hydrogenation from 1.15 g of the compound from Example 34 (2.1 mmol), 55 ml of methanol, 5.9 ml of methanolic hydrogen chloride solution (3.2 mmol) and 0.11 g of palladium/activated carbon analogously to the working directions for Example 17.

The base does not crystallize from diisopropyl ether in this case and was therefore precipitated as the hydrochloride by adding ethereal hydrogen chloride solution dropwise. The precipitate was filtered off with suction and dried at 50° C./0.1 mb. A white solid is obtained.

Yield: 0.70 g=70% of theory

M.p.: 130° C./157°–158° C.

$R_f$=0.40 (silica gel; toluene/methanol 85:15)

EXAMPLE 36

2-{N-Benzyl-N-[3-(N-methyl-4-fluorophenylsulphonamido)propyl] aminomethyl}-8-methoxytetralin

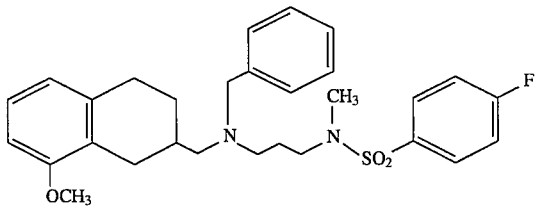

The compound is prepared from 3.97 g of the compound from Example 16 (8 mmol), 211 mg of sodium hydride (8,8 mmol) and 1.14 g of methyl iodide (8 mmol) in dry dimethyl formamide analogously to the working directions for Example 34.

The crude product is chromatographed on 250 g of silica gel 60 using diisopropyl ether. A colorless resin is obtained.

Yield: 4.03 g=99% of theory $R_f$=0.47 (silica gel, diisopropyl ether)

EXAMPLE 37

2-{N-[2-(2-Carboxamido-N-(8-methoxytetralin-2-yl-methyl)phenylsulphonamido)ethyl]aminomethyl}-8-methoxytetralin

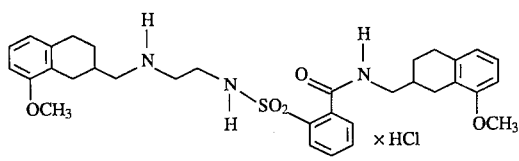

1.90 g of the compound from Example 6 (10 mmol), 1.00 g of triethylamine (10 mmol) and 2.90 g of 2-(2-bromobutyl)- 1,2-benzisothiazol-3(2H)-one 1,1-dioxide are stirred for 24 h at 40° C. in 38 ml of dimethylformamide.

For working up, the mixture is stirred into a mixture of 380 ml of 5% strength sodium chloride solution, 130 ml of toluene and 10 ml of 1N hydrochloric acid, the final product being precipitated as the resinous hydrochloride. The liquid phases are poured off and 400 ml of 5% strength sodium chloride solution and 130 ml of toluene are added to the resin. 1N sodium hydroxide solution is then cautiously added dropwise with stirring, the pH being kept at a maximum of 11. The organic phase is then washed with water until neutral and dried over sodium sulphate. The solvent is then distilled off at 30° C. and 40 mb.

The crude product obtained is chromatographed on 90 g of silica gel 60 using ethyl acetate. A yellow resin is obtained.

The base can be precipitated as the hydrochloride from toluene solution by adding ethereal hydrogen chloride solution dropwise.

Yield: 1.51 g=51% of theory $R_f$=0.32 (silica gel; toluene/methanol 85:15)

$R_f$=0.15 (ethyl acetate)

EXAMPLE 38

2-{N-[3-(N-Methyl-4-fluorophenylsulphonamido)-propyl]aminomethyl}- 8-methoxytetralin

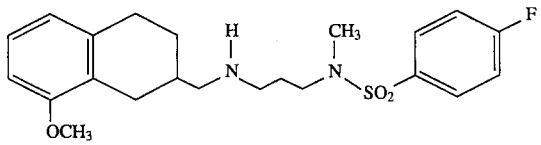

The compound is obtained as a viscous oil after hydrogenation from 3.90 g of the compound from Example 36 (7.6 mmol), 195 ml of methanol, 21 ml of methanolic hydrogen chloride solution (11.4 mmol) and 0.38 g of palladium/activated carbon analogously to the working directions for Example 17.

The base crystallizes from diisopropyl ether. A white solid is obtained.

Yield: 2.15 g=67% of theory; M.p.: 66°–67° C.

$R_f$=0.23 (silica gel; toluene/methanol 85:15)

EXAMPLE 39

2-{N-Benzyl-N-[3-(phenylcarboxamido)propyl]-aminomethyl}- 8-methoxytetralin

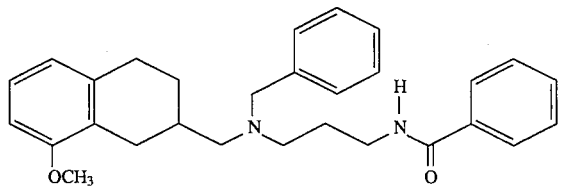

The compound was prepared from 3.39 g of the compound from Example 9 (10 mmol), 1.38 g of potassium carbonate (10 mmol) and 1.41 g of benzoyl chloride (10 mmol) in dichloromethane analogously to the working directions for Example 16.

The crude product was chromatographed on 90 g of silica gel 60 using diisopropyl ether (dissolved in a little toluene for application). The pure product then crystallized out from the main fraction. The crystallisate was filtered off with suction and dried at 50° C./1 mb. A white crystallisate was obtained.

Yield: 3.6 g=82% of theory

M.p.: 95.5°–96.5° C.

$R_f$=0.10 (silica gel; toluene/methanol 85:15)

$R_f$=0.10 (diisopropyl ether)

EXAMPLE 40

2-{N-Benzyl-N-[3-(N-benzyl-phenylcarboxamido)-propyl]aminomethyl}- 8-methoxytetralin

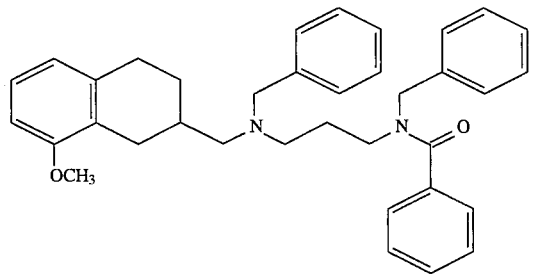

The compound is prepared from 1.77 g of the compound from Example 39 (4 mmol), 106 mg of sodium hydride (4.4 mmol) and 0.68 g of benzyl bromide (4 mmol) in dry dimethylformamide analogously to the working directions for Example 34.

The crude product is chromatographed on 90 g of silica gel 60 using diisopropyl ether. A colorless resin is obtained.

Yield: 1.73 g=81% of theory $R_f$=0.28 (silica gel; diisopropyl ether)

EXAMPLE 41

2-{N-Benzyl-N-[3-(N-methyl-phenylcarboxamido)-propylaminomethyl}- 8-methoxytetralin

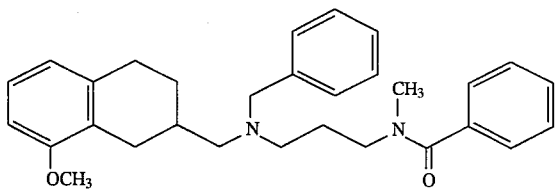

The compound is prepared from 1.77 g of the compound from Example 39 (4 mmol), 106 ml of sodium hydride (4.4 mmol) and 0.57 g of methyl iodide (4 mmol) in dry dimethylformamide analogously to the working directions for Example 34.

The crude product is chromatographed on 250 g of silica gel 60 using diisopropyl ether/methanol 95:5. A colorless resin is obtained.

Yield: 1.62 g=89% of theory $R_f$=0.52 (silica gel; toluene/methanol 90:10)

EXAMPLE 42

2-{N-[3-(N-Benzyl-phenylcarboxamido)propyl]-aminomethyl}- 8-methoxytetralin

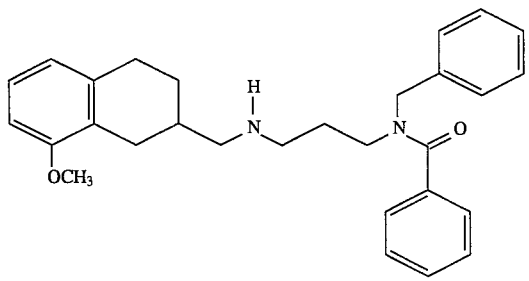

The compound is obtained as a viscous oil after hydrogenation from 1.68 g of the compound from Example 40 (3.2 mmol), 84 ml of methanol, 8.9 ml of methanolic hydrogen chloride solution (4.8 mmol) and 0.16 g of palladium/activated charcoal analogously to the working directions for Example 17.

The base is converted into the hydrochloride.

A white solid is obtained.

Yield: 1.18 g=76% of theory $R_f$=0.32 (silica gel; toluene/methanol 85:15)

EXAMPLE 43

2-{N-[3-(N-Methyl-phenylcarboxamido)propyl]-aminomethyl}- 8-methoxytetralin

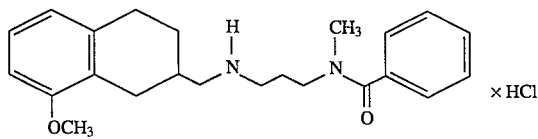

The compound is obtained as a viscous oil after hydrogenation from 1.46 g of the compound from Example 41 (3.2 mmol), 73 ml of methanol, 8.9 ml of methanolic hydrogen chloride solution (4.8 mmol) and 0.16 g of palladium/activated charcoal analogously to the working directions for Example 17.

The base is converted into the hydrochloride analogously to the working directions of Example 19.

A white solid is obtained.

M.p.: 128°–130° C.

$R_f$=0.38 (silica gel; toluene/methanol 70:30)

$R_f$=0.28 (base)

EXAMPLE 44

2-{N-[3-(Phenylcarboxamido)propyl]aminomethyl}- 8-methoxytetralin

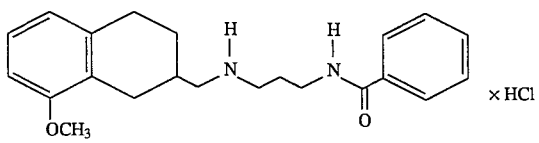

The compound is obtained as a viscous oil after hydrogenation from 1.20 g of the compound from Example 39 (2.7 mmol), 60 ml of methanol, 7.6 ml of methanolic hydrogen chloride solution (4.1 mmol) and 0.14 g of palladium/activated charcoal analogously to the working directions for Example 17.

The base is converted into the hydrochloride analogously to the working directions of Example 19.

A white solid is obtained.

M.p.: 134.5°–137° C.

$R_f$=0.35 (silica gel; toluene/methanol 70:30)

$R_f$=0.22 (base)

EXAMPLE 45

2-{N-Methyl-N-[3-(N-methyl-4-fluorophenyl-sulphonamido)propyl] aminomethyl}-8-methoxytetralin

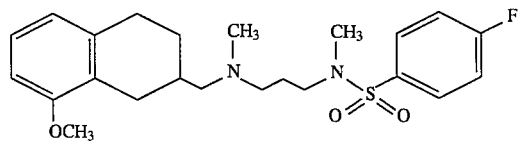

The compound is prepared from 1.05 g of the compound from Example 38 (2.5 mmol), 0.12 g of acetic acid (1.88 mmol), 0.19 g of sodium cyanoborohydride (3.0 mmol), 33 ml of methanol and a solution of 0.21 g of 37% strength aqueous formaldehyde solution (2.5 mmol) in 5 ml of methanol analogously to the working directions for Example 7.

The base is obtained as a colorless viscous oil.

Yield: 1.03 g=95% of theory $R_f$=0.47 (silica gel, toluene/methanol 85:15).

EXAMPLE 46

2-{N-[4-(1,1-Dioxido-3-oxo-2,3-dihydro-benzisothiazol-2-yl)butyl] aminomethyl}quinoline

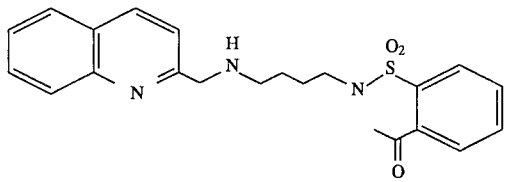

A solution of 8.91 g (28 mmol) of 2-(4-bromobutyl)-1,2-benzoisothiazol-3(2H)-one 1,1-dioxide in 30 ml of anhydrous dimethylformamide is added dropwise to a mixture of 4.9 g (31 mmol) of 2-aminomethylquinoline and 2.8 g (28 mmol) of triethylamine in 100 ml of anhydrous dimethylformamide and the mixture is stirred at 40° C. for 14 h. The mixture is then poured into 600 ml of water and extracted using ethyl acetate, and the organic phase is washed with water and dried over sodium sulphate. After filtering and evaporating off the solvent, 8 g of a brown, viscous oil which is purified by column chromatography on silica gel (eluent: methylene chloride/methanol/conc. ammonia solution (10:0.1:0.1)) are obtained.

Yield: 1.75 g=16% of theory, yellow oil.

$R_f$=0.32 (silica gel; methylene chloride/methanol 100:5).

$^1$H-NMR (CD$_2$Cl$_2$): 1.65–1.72 (m; —CH$_2$—CH$_2$—; 2H), 1.9–2.0 (m; —CH$_2$—; 2H), 2.3–2.6 (m; NH), 2.8 (t; NH—CH$_2$—; 2H), 3.82 (t; —CON—CH$_2$; 2H), 4.09 (s; NH—CH$_2$—ar; 2H), 7.45–8.15 (m; ar; 10H).

The base can be precipitated from methanolic solution as the naphthalene-1,5-disulphonic acid salt by adding equimolar amounts of methanolic naphthalene-1,5-disulphonic acid solution dropwise. M.p.: 224° C.

EXAMPLE 47

2-{N-[4(1,1-dioxido-2,3-dihyro-benzisothiazol-2-yl)butyl] aminomethyl}-8-methoxy-tetralin

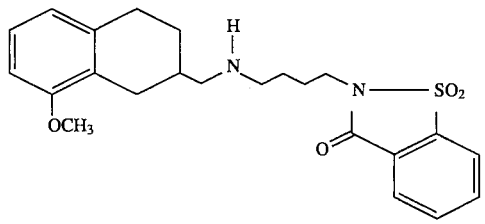

2 g of 2-aminomethyl-8-methoxytetralin (10.5 mmol), 3.2 g of 2-(4-bromobutyl)-1,2-(2H)benziosothiazole 1,1-dioxide (10.5 mmol) and 1.46 ml of triethylamine (10.5 mmol) are stirred at 40° C. for 24 h in 40 ml of dimethylformamide. The reaction solution is then stirred into a mixture of 440 ml of water and 140 ml toluene. The organic phase is washed with water and dried over sodium sulphate. The solvent is distilled off in vacuo. The residue is purified by column chromatography on silica gel 60 (Merck) using toluene/methanol 70:30. The residue obtained after distilling off the solvent from the main fraction crystallizes after triturating with ether.

Yield: 900 mg=21% of theory

M.p.: 94°–95° C.

TLC: $R_f$=0.3 Silica gel/toluene-methanol 70:30

EXAMPLE 48

2-{N-[4-(N-methyl-4-fluorophenylsulphonamido)butyl] aminomethyl}-8-methoxy-tetralin

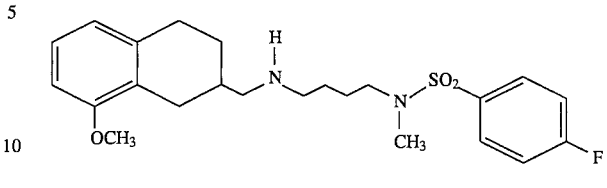

The compound is prepared from 1 g of 2-aminomethyl-8-methoxytetralin (5.2mmol), 1.7 g of N-methyl-N-(4-bromobutyl)- 4-fluorophenylsulphonamide (5.2 mmol) and 0.73 ml of triethylamine (5.2 mmol) in 20 ml of dimethylformamide analagously to the working directions of Example 47.

The final product is precipitated from ethereal solution as the hydrochloride using ethereal hydrogen chloride solution.

Yield: 400 mg=16% of theory

M.p.: 144° C.

TLC: $R_f$=0.44 Silica gel/toluene-methanol 70:30

EXAMPLE 49

2-{N-[4-N-methyl-napthalenyl-2-sulphonamido)butyl]-aminomethyl}- 8-methoxy-tetralin

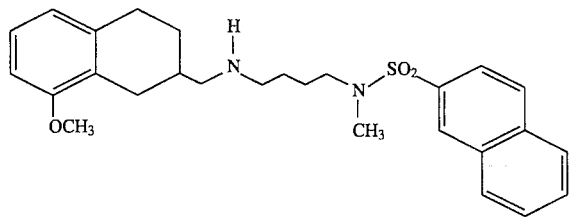

The compound is prepared from 1 g of 2-aminomethyl-8-methoxytetralin (5.2 mmol), 1.9 g-of N-methyl-N-(4-bromobutyl)-naphthalene- 2-sulfonamide (5.2 mmol) and 0.73 ml of triethylamine (5.2 mmol) in 20 ml of dimethylformamide analogously to the working directions of Example 47.

The final product is chromatographed on silica gel using toluene/methanol 85:15.

The final product is dissolved in dichloromethane and precipitated as the hydrochloride using ethereal hydrogen chloride solution.

Yield: 900 mg=35% of theory

M.p.: 194°–196° C.

TLC:

$R_f$=0.13 Silica gel/toluene-methanol 85:15

EXAMPLE 50

2-{N-[4-(N-methyl-naphthalenyl-1-sulfonamido)-butyl]aminomethyl}- 8-methoxy-tetralin

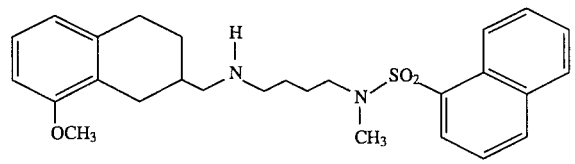

The compound is prepared from 2 g of 2-aminomethyl-8-methoxytetralin (10.5 mmol), 3.7 g of N-methyl-N-(4-bromobutyl)-naphthalene- 2-sulfonamide (10.5 mmol) and 1.46 ml of triethylamine (10.5 mmol) in 40 ml of dimethylformamide analogously to the working directions of Example 47.

The final product is chromatographed on silica gel using ethanol.

The final product is dissolved in ethanol and precipitated as the hydrochloride using ethereal hydrogen chloride solution.

Yield: 1.0 g=19% of theory

M.p.: 161°–164° C.

TLC: $R_f$=0.45 Silica gel/toluene-methanol 70:30

EXAMPLE 51

2-{N-[4-(N-pyridinyl-2-methanesulfonamido)-butyl]-aminomethyl}- 8-methoxy-tetralin

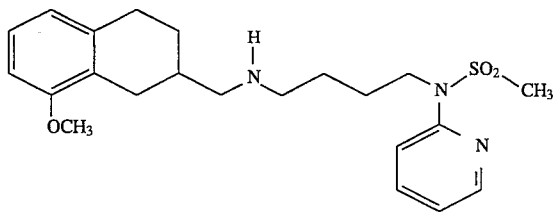

1.60 g of 2-aminomethyl-8-methoxytetralin (8.4 mmol), 2.28 g of N-(4-bromobutyl)-pyridinyl-2-methanesulfonamide (7.4 mmol) and 0.85 g of triethylamine (8.4 mmol) are stirred under argon at 40° C. for 24 h in 32 ml of dimethylformamide.

The reaction solution is then stirred into a mixture of 160 ml of 5% strength sodium chloride solution, 80 ml of toluene and 8.5 ml of 1N sodium hydroxide solution. The organic phase is washed once with 40 ml of water and dried over sodium sulfate.

After the solvent has been distilled off in vacuo, the crude product obtained is chromatographed on silica gel 60 (Merck) using methanol.

Yield: 1.9 g=61% of theory

TLC: $R_f$=0.25 Silica gel/methanol

EXAMPLE 52

2-{4-[2-(methylsulfonylimino]-1,2-dihydropyridin-1-yl]-butylaminomethyl} 8-methoxy-1,2,3,4-tetrahydro-naphthalene

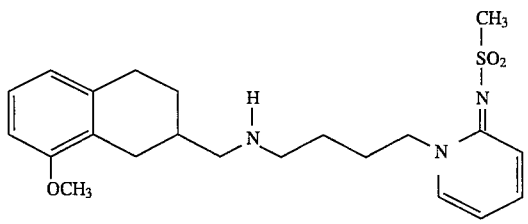

The compound is prepared from 1.60 g of 2-aminomethyl-8-methoxytetralin (8.4 mmol), 2.28 g of 1-(4-bromobutyl)-2-methylsulfonylimino- 1,2-dihydropyridine (7.4 mmol) and 0.85 ml of triethylamine (8.4 mmol) in 32 ml of dimethylformamide analogously to the working directions of Example 51.

Yield: 2.1 g=68% of theory

TLC: $R_f$=0.15 Silica gel/toluene-methanol 70:30 $R_f$=0.43 Silica gel/methanol-triethylamine 95:5

EXAMPLE 53

2-{N-[4-(1,1-dioxido-3-oxo-2,3-dihydro-benzisothiazol-2-yl)pentyl] amino}-8-methoxy-chroman Hydrochloride

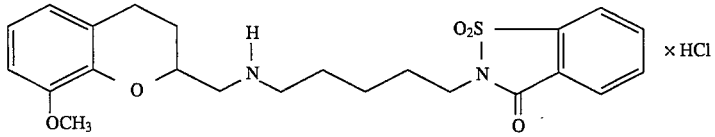

The title compound was prepared in analogy to the directions for Example 20.

M.p.: 110° C.–118° C. (after sintering)

EXAMPLE 54

2-{N-[2-N-methyl-4-fluorophenylsulfonamido)-ethyl]aminomethyl} chroman Hydrochloride

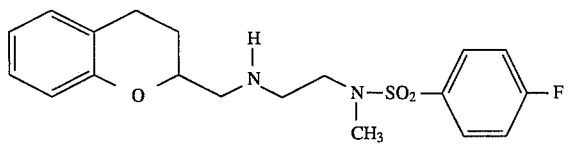

The title compound was prepared in analogy to the directions for Example 20.

M.p.: 143° C.–155° C.

EXAMPLE 55

2-{N-[4-(5,5-dioxido-6H-dibenzo[c,1][1,2]thiazin-6-yl)butyl} aminomethylchroman-1,5-naphthalenedisulfonic Acid Salt (Stoichiometry 2:1)

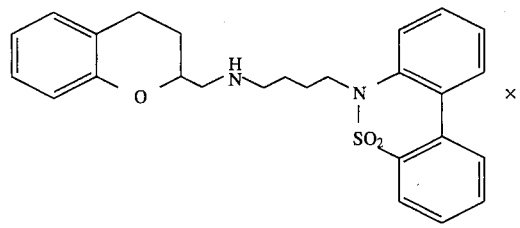

The free base [R$_f$(CH$_2$Cl$_2$/CH$_3$OH) 10:1]=0.39] was converted into the 2:1 salt in acetone/ether by treating with 1,5-naphthalenedisulfonic acid. Pale beige solid.

M.p.: >240° C. (decomposition)

The compound of Example 56 was additionally obtained in the reaction.

EXAMPLE 56

2-{N,N-bis(5,5-dioxido-6H-dibenzo[c,e][1,2]-thiazin-6yl)butyl} aminomethylchroman-1,5-naphthalenedisulfonic Acid Salt (2:1)

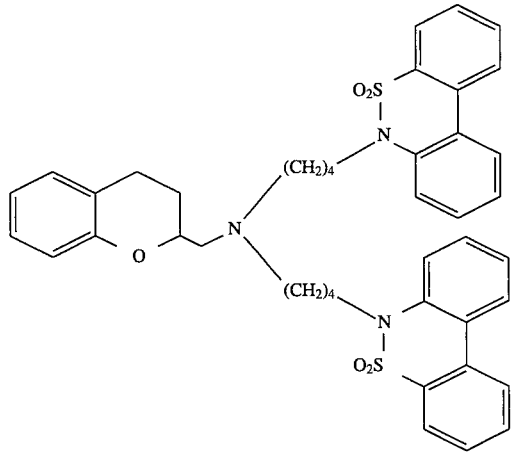

The free base was obtained as a non-polar component in addition to the compound of Example 55; R$_f$(CH$_2$Cl$_2$/CH$_3$OH 10:1)=0.91.

The 2:1 salt with 1,5-naphthalenedisulfonic acid was obtained as in Example 55 (colorless solid). M.p.: from 170° C. (decomposition),

EXAMPLE 57

2-{N-[4-(5,5-dioxido-6H-dibenzo[c,e][1,2]-thiazin-6-yl)butyl]} aminomethyl-8-methoxyychroman Hydrochloride

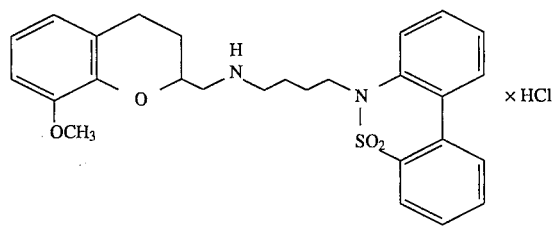

The free base [R$_f$(CH$_2$Cl$_2$/CH$_3$OH 10:1=0.25] gave the hydrochloride as an amorphous, beige solid after treating with ethereal hydrogen chloride in methanol.

EXAMPLE 58

2-{N-[4(1,1-dioxido-2H-naphth[1,8-cd]isothiazol-2-yl)butyl]} aminomethyl-8-methoxy-chroman Hydrochloride

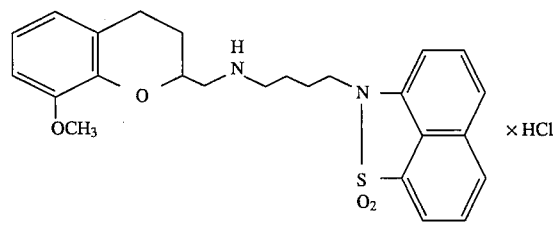

The free base [R$_f$(CH$_2$Cl$_2$/CH$_3$OH 10:1)=0.3] gave the hydrochloride as slightly greenish crystals after treating with ethereal hydrogen chloride in ethyl acetate.

M.p.=159°–162° C.

EXAMPLE 59

2-{N-[3-(1,3-dimethyl-uracil-6-yl)amino]-propyl}aminomethyl- 8-methoxy-chroman Hydrochloride

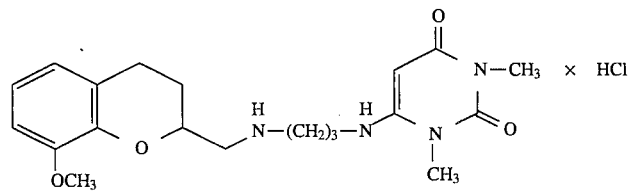

The title compound was prepared in analogy to the directions for Example 20.

The free base (R$_f$(CH$_2$Cl$_2$/CH$_3$OH 10:1)=0.19], dissolved in methanol, was treated with ethereal hydrogen chloride. After addition of ether, the hydrochloride was obtained as a colorless solid. M.p.: from 195° C. with decomposition (foaming).

M.p.: 135°–138° C.

EXAMPLE 62

2-{N-[4(4-fluorophenylsulfonamido)-butyl]}aminomethyl-chroman Hydrochloride

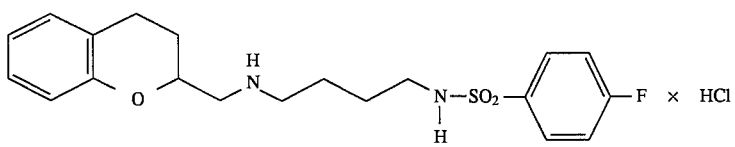

EXAMPLE 60

2-{N-[4-(2,3-dihydro-1,1-dioxido-benzisothiazol-2-yl)butyl]} amino-methyl-chroman Hydrochloride

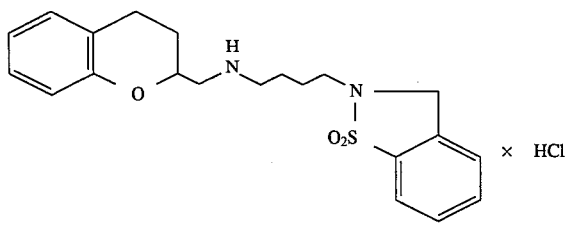

The title compound was prepared in analogy to the directions for Example 20.

The free base [R$_f$(CH$_2$Cl$_2$/CH$_3$OH 10:1)=0.49] was converted into the hydrochloride and recrystallized from isopropanol.

M.p.: 215°–23.6°.

EXAMPLE 61

2-{N-[4-(2,3-dihydro-1,1-dioxido-benzisothiazol-2-yl)butyl]} amino-methyl-8-methoxy-chroman Hydrochloride

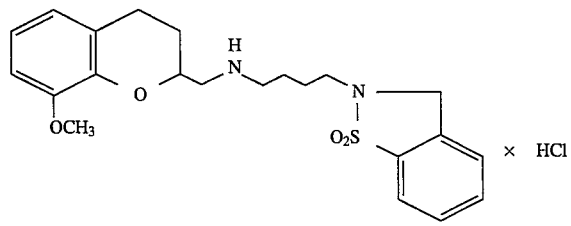

The title compound was prepared in analogy to the directions for Example 20.

The free base [R$_f$(CH$_2$Cl$_2$/CH$_3$OH 10:1)=0.27] was dissolved in methanol and treated with ethereal hydrogen chloride, and the hydrochloride precipitated after addition of ether was recrystallized from ethyl acetate.

The title compound was prepared in analogy to the directions for Example 24.

M.p. 202°–206° C.

The compounds (63 to 70) listed in table 1 were prepared according to the following method of procedure: 1.89 g of 8-methoxy-2-aminomethyl-1,2-dihydronaphthalene (10 mmol), ×g of I (10 mmol) and 1.39 ml of triethylamine (10 mmol) are stirred in 19 ml of dimethylformamide under an argon atmosphere for 24 hours at 40° C.

Then the reaction solution is poured slowly into a stirred mixture of 90 ml of a 5% strength sodium chloride solution, 10 ml of 1N sodium hydroxide solution and 50 ml of toluene. The mixture is stirred for a further 10 minutes; after which the organic phase is separated off. The aqueous phase is extracted once more with 25 ml of toluene. The combined organic phases are washed twice with 25 ml of water, dried over sodium sulphate and the solvent is distilled off in vacuo at 40° C.

The crude product obtained is purified by column chromatography on silica gel using ethanol (examples 63 to 67) or ethyl acetate (examples 68 to 70) as the mobile solvent.

The clean base is dissolved in ether/ethanol in a ratio of 90:10 (examples 63 to 67) or ether (examples 68 to 70) and precipitated in the form of the hydrochloride using an ethereal hydrogen chloride solution.

The yields are in between 30 and 40% of theory.

TABLE 1

[Structure: 8-methoxy-3,4-dihydronaphthalene-2-yl-CH2-NH-Y-Z]

| Example No.: | Y—X | Rf-value on silica gel using toluene/methanol in a ratio of 70:30 | M.p.: |
|---|---|---|---|
| 63 | pentyl-N(SO2-2-benzoyl)- (cyclic, 2-acylbenzenesulfonamide) | 0,48 | 180° C. |
| 64 | pentyl-N(SO2-o-tolyl-CH2-) (cyclic) | 0,38 | 150–152° C. |
| 65 | butyl-N fused to benzisothiazoline-1,1-dioxide | 0,40 | 196–198° C. |
| 66 | propyl-N(SO2-o-tolyl-CH2-) (cyclic) | 0,58 | 183–185° C. |
| 67 | pentyl-N, naphthalene-1,8-sultam | 0,48 | — |
| 68 | pentyl-N(CH3)-SO2-(2-naphthyl) | 0,48 | — |
| 69 | pentyl-N(CH3)-SO2-(1-naphthyl) | 0,48 | 129–133° C. |

TABLE 1-continued

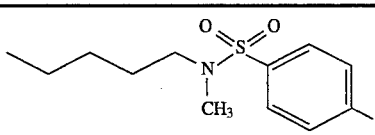

| Example No.: | Y—X | Rf-value on silica gel using toluene/methanol in a ratio of 70:30 | M.p.: |
|---|---|---|---|
| 70 | (structure: pentyl-N(CH₃)-SO₂-C₆H₄-F) | 0,43 | 125° C. |

Examples 71 and 72 listed below were prepared by an analogous procedure to that used for Examples 65 and 66 from 8-methoxy-2-aminomethyl-1,2,3,4-tetrahydronaphthalene, 2-(3-bromopropyl-1-yl)benzisothiazole-1,1-dioxide, and 2-(2-bromometh-1-yl)-benzisothiazole-1,1-dioxide and triethylamine in dimethylformamide.

EXAMPLE 71

8-Methoxy-2-aminomethyl-N[3-benzisothiazole-1,1-dioxid-2-yl)propyl]-1,2,3,4-tetrahydronaphthalene

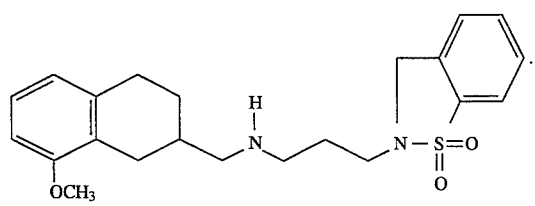

$R_F$=0,393 (hydrochloride), on silica gel using toluene/methanol (70:30)

M.p.: 166°–168° C. (hydrochloride)

Yield: 27% of theory

EXAMPLE 72

8-Methoxy-2-aminomethyl-N[2-(benzisothiazole, 1,1-dioxid-2-yl)ethyl-1]-1,2,3,4-tetrahydronaphthalene

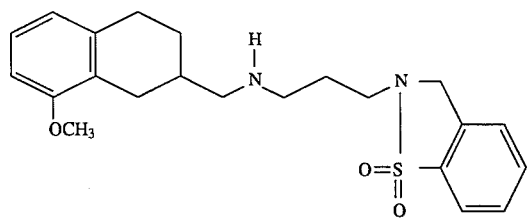

$R_F$=0,483 (hydrochloride), on silica gel using toluene/methanol (70:30)

M.p.: 236°–238° C.

Yield: 38% of theory

The compounds listed in Table 2 were prepared following the same procedure as that described in Example 20:

TABLE 2

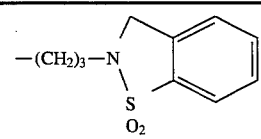

| Example No.: | Y—Z | TLC/Rf-value or MS | M.p.: | Salt |
|---|---|---|---|---|
| 73 | —(CH₂)₃—N(benzisothiazole-SO₂) | | 195–197 | × HCL |

TABLE 2-continued

Structure: 2-methoxyphenyl-chroman with side chain -CH$_2$-NH-Y-Z (OCH$_3$ on aromatic ring, O in ring)

| Example No.: | Y—Z | TLC/Rf-value or MS | M.p.: | Salt |
|---|---|---|---|---|
| 74 | —(CH$_2$)$_2$—N(benzisothiazole-S,S-dioxide) | 0,50 CH$_2$Cl$_2$/CH$_3$OH (10:1) | | |
| 75 | —(CH$_2$)$_4$—N(isothiazolidine-S,S-dioxide) | | | |
| 76 | —(CH$_2$)$_3$—N(isothiazolidine-S,S-dioxide) | | | |
| 77 | —(CH$_2$)$_2$—N(isothiazolidine-S,S-dioxide) | | | |
| 78 | —(CH$_2$)$_4$—N(piperidinyl-SO$_2$) | MS: (free base) 382, 219 (100%) 84 | | |
| 79 | —(CH$_2$)$_4$—N(benzo-fused-SO$_2$-ring) | MS: (free base) 430, 267 (100%) amorph 105, 86, 84 | | |
| 80 | —(CH$_2$)$_3$—N(benzo-fused-SO$_2$-ring) | | | |
| 81 | —(CH$_2$)$_2$—N(benzo-fused-SO$_2$-ring) | 0,16 CHCl$_2$/ C$_3$H$_8$OH (20:1) | 158–159 | Oxalate |

The compounds listed in tables 3, 4 and 5 were prepared following the same procedure as that described in Example 20:

TABLE 3

[Structure: 5-fluoro-8-cyano-chroman with -CH2-NH-Y-Z × HCl substituent at 2-position]

| Example No.: | Y—Z | TLC/Rf-value on silica gel using toluene/methanol (70:30)* or ethanol** | M.p.: |
|---|---|---|---|
| 82 | pentyl-N(C(=O))-(2-methanesulfonyl-phenyl), N-SO2 | 0.25** | 109–111° C. |
| 83 | propyl-N(CH2-2-phenyl)-SO2 | 0.49* | 199–201° C. |
| 84 | butyl-N(CH2-2-phenyl)-SO2 | | |
| 85 | pentyl-N(CH2-2-phenyl)-SO2 | 0.38* | 216–218° C. |

TABLE 4

Structure: 5-fluoro-substituted benzene with CO-NH₂ group, connected via -CH₂CH₂-C(=O)-CH₂-NH-Y-Z × HCl

| Example No.: | Y—Z | TLC/Rf-value on silica gel/ethanol | M.p.: |
|---|---|---|---|
| 86 | pentyl-N(C(=O)-)-SO₂-phenyl (2-substituted) | 0,28 | 140–142° C. |
| 87 | propyl-N(CH₂-phenyl)-SO₂ (2-substituted benzyl sulfonamide) | | |
| 88 | butyl-N(CH₂-phenyl)-SO₂ (2-substituted benzyl sulfonamide) | | |
| 89 | hexyl-N(CH₂-phenyl)-SO₂ (2-substituted benzyl sulfonamide) | | |

TABLE 5

Structure: benzene with OC₂H₅ group, connected via -CH₂CH₂-C(=O)-CH₂-NH-Y-Z × HCl

| Example No. | Y—Z | TLC/Rf-value | M.p.: |
|---|---|---|---|
| 90 | butyl-N(C(=O)-)-SO₂-phenyl | 0,38 ClCH₂CH₂Cl/1PrOH 10:1 | 185° C. |
| 91 | butyl-N(CH₂-phenyl)-SO₂ | 0,22 ClCH₂CH₂Cl/1PrOH 10:1 | 153° C. |

EXAMPLE 92

(+)-2-{N-[4-(1,1-Dioxido-3-oxo-2,3-dihydro-benzisothiazol-2-yl)butyl] aminomethyl-chroman and (−)-2-{N-[4-(1,1-Dioxido-3-oxo-2,3-dihydro-benzisothiazol-2-yl)butyl] aminomethyl-chroman

EXAMPLE 92a

Chroman-2-carboxylic Acid Chloride

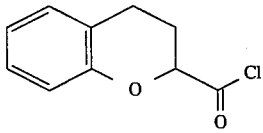

89.0 g (0.5 mol) chroman-2-carboxylic acid and 71.4 g (0.6 mol) thionyl chloride were heated to 80° for 4–5 hours (end of gas evolution). Destillation (77°–80°/0.1 torr) yielded 96.0 g (98%) chroman-2-carboxylic acid chloride

EXAMPLE 92b

N-[1-(S)-Phenethyl]-chroman-2-carboxamide
(Diastereomers)

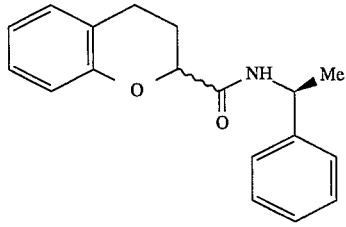

39.9 g (0.33 mol) (S)-(−)-1-phenylethylamine and 30.9 g. (0.3 mol) triethylamine were added dropwise with stirring to a solution of 59.0 g (0.3 mol) chromane-2-carboxylic acid chloride (ex. 92a) in 200 ml dichloromethane. After stirring over night, the reaction mixture was poured on ice. Phases were separated, the organic phase was washed with brine and dried over anhydrous sodium sulfate, yielding 87.8 g crude N-[1-(S)-phenethyl]-chroman- 2-carboxamide as a 1:1 mixture of diastereomers. Repeated crystalization (4×) from ethanol furnished 15.8 g of a single diasteromer (d.e. ≧99.5%). m.p. 127°–128° C.; $\alpha_D$=+17.5 (c=1, tetrahydrofuran).

| $C_{18}H_{19}NO_2$ | calc. | C 76.84 | H 6.81 | N 4.98 |
|---|---|---|---|---|
| (281.4) | found | 76.9 | 7.18 | 4.97 |

Evaporation of the mother liquors yielded 61.2 g of a mixture of diasteromers.

EXAMPLE 92c

N-[1-(R)-phenethyl]-chroman-2-carboxamide
(Diastereomers)

| $C_{18}H_{19}NO_2$ | calc. | C 76.84 | H 6.81 | N 4.98 |
|---|---|---|---|---|
| (281.4) | found | 76.8 | 7.22 | 5.17 |

In analogy to example 92b, 15 g of a single diasteromer (d.e.= 100%) was obtained by starting from (R)-(+)-1-phenylethylamine.

m.p. b 127°128° C.; $\alpha_D$=−17.2 (c=1, tetrahydrofuran).

| $C_{18}H_{19}NO_2$ | calc. | C 76.84 | H 6.81 | N 4.98 |
|---|---|---|---|---|
| (281.4) | found | 76.8 | 7.22 | 5.17 |

EXAMPLE 92d

N-[1-(S)-phenethyl]-2-aminomethylchroman
(Diastereomer A)

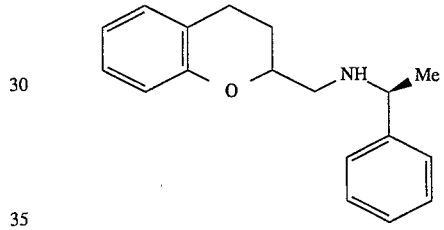

At 0° C. a solution of 16.2 g (0.058 mol) of the pure diasteromer of N-[1-(S)-phenethyl]-chroman-2-carboxamide ($\alpha_D$=+17.5°; from example 92b) in 300 ml anhydrous tetrahydrofuran was added dropwise with stirring to a solution of 0.2 mol diborane in 400 ml anhydrous tetrahydrofuran. The reaction mixture was stirred overnight at 20° and then heated to reflux for 1 hour. 10% hydrochloric acid was added cautiously to the cold reaction mixture. The solvent was removed in vacuo. The residue was brought to pH ~8.5 with dilute sodium hydroxide and then extracted with diethylether. The combined organic extracts were washed with brine and dried over anhydrous sodium sulfate. Evaporation yielded 17.4 g crude N-[1-(S)-phenethyl]-2-aminomethyl-chroman with a d.e. >99.5%. An analytical sample was obtained by Kugelrohr destillation (190° C./0.02 torr).

| $C_{18}H_{21}NO$ | calc. | C 80.86 | H 7.92 | N 5.24 |
|---|---|---|---|---|
| (267.4) | found | 80.7 | 8.01 | 5.41 |

EXAMPLE 92e (+)-N-[1-(S)-phenethyl]-2-aminomethylchroman
(Diastereomer B)

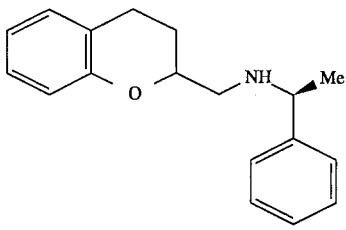

In analogy to example 92d, 42.2 g of the mixture of diastereomers obtained in example 92b (after the separation of a pure diastereomer by crystallization) yielded after reaction with 0.3 mol diborane, 42.8 g of a crude mixture of N-[1-(S)-phenethyl]- 1-aminomethylchroman diastereomers. This material was chromatographed on 600 g of silica, using toluene/ethyl acetate as eluents. This gave 9.0 g of a pure diastereomer, which was identical with the one obtained in example 92d as well as 25.4 g of a less polar N-[1-(S)-phenethyl]- 2-aminomethylchroman, d.e. >99.5% (diastereomer B). An analytical sample hereof was obtained by Kugelrohr destillation (195° C./0.05 torr).

$\alpha_D$=+42.3 (C=1, tetrahydrofuran)

| $C_{18}H_{21}NO$ | calc. | C 80.86 | H 7.92 | N 5.24 |
|---|---|---|---|---|
| (267.4) | found | 80.7 | 8.08 | 4.97 |

EXAMPLE 92f (−)-2-Aminomethyl-chroman

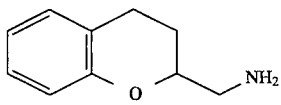

27.5 g (0.1 mol) pure N-[1-(S)-phenethyl]-2-aminomethylchroman (from example 92d) in 400 ml ethanol were hydrogenated for 24 h at 50°/10 bar, using 5% Pd/C catalyst. Filtration over silica with toluene/ethylacetate, followed by methanol, furnished 12.5 g 2-aminomethylchroman enantiomer.

boiling range: 100°–110° C./0.04 torr (Kugelrohr)

e.e.: >97.5%

$\alpha_D$=−122.8° (c=1, tetrahydrofuran)

| $C_{10}H_{13}NO$ | calc. | C 73.59 | H 8.03 | N 8.58 |
|---|---|---|---|---|
| (163.2) | found | 73.7 | 8.39 | 8,85 |

EXAMPLE 92g (+)-2-Aminomethyl-chroman

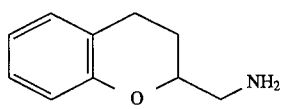

In analogy to example 92f, 21.5 g (0.08 mol) (+)-N-[1-(S)-phenethyl]-2-aminomethylchroman (example 92e; $\alpha_D$= 42.3) was hydrogenated in 400 ml ethanol (Pd/C 5%). Thus 10.2 g homogeneous (+)-2-aminomethylchroman was obtained;

boiling range: 100°–110° C./0.03 torr (Kugelrohr)

e.e.: ≧97.0%

$\alpha_D$=+128.8° (C=1, tetrahydrofuran)

| $C_{10}H_{13}NO$ | calc. | C 73.59 | H 8.03 | N 8.58 |
|---|---|---|---|---|
| (163.2) | found | 73.3 | 8.11 | 8.82 |

EXAMPLE 92h

2-{N-[4-(1,1-Dioxido-3-oxo-2,3-dihydro-benzisothiazol-2-yl)butyl] aminomethyl)chroman and its hydrochloride [(−)-isomer]

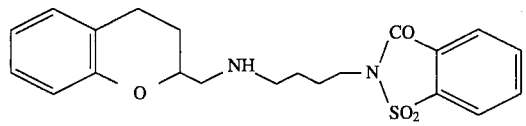

The mixture of 5.4 g (0.033 mol) (−)-2-aminomethylchroman (example 92f; $\alpha_D$=−122.8), 6.1 g (0.06 mol) triethylamine, 9.5 g (0.03 mol) N-(4-bromobutyl) saccharin and 80 ml anhydrous dimethyl formamide was heated to 60° C. for 4 h. The solvent was evaporated at 0.01 torr. The residue (13.5 g) was dissolved in toluene/ethyl acetate (5:1) and chromatographed on silica (300 g). The fraction (5.8 g) obtained by elution with toluene/ethyl acetate 1:1 was rechromatographed on 150 g of silica, providing 3.7 g of chemically pure 2-(N-[4-(1,1-Dioxido-3-oxo-2,3-dihydro-benzisothiazol- 2-yl)butyl]aminomethyl)chroman.

Hydrochloride m.p. (closed capillary): 192°–194° C.

e.e.: ≧99%

$\alpha_D$=−42.2 (C=1, trichloromethane)

| $C_{21}H_{24}N_2O_4S \times HCl$ | calc. | C 57.72 | H 5.78 | N 6.41 |
|---|---|---|---|---|
| (437) | found | 57.5 | 5.81 | 6.40 |

EXAMPLE 92i

2-{N-[4-(1,1-Dioxido-3-oxo-2,3-dihydro-benzisothiazol-2-yl)butyl] aminomethyl)chroman and Its Hydrochloride [(+)-isomer]

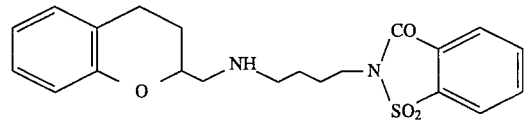

5.4 g (0.033 g) (+)-2-aminomethylchromane from example 92g ($\alpha_D$= +122.8°) was reacted with N-(4-bromobutyl) saccharin in analogy to example 92h. After chromatography of the crude product (11.6 g) on silica with toluene/ethyl acetate (5:1 to 2:1), the resulting material (5.4 g) was rechromatographed on 175 g silica. This lead to 4.2 g pure 2-{N-[4-(1,1-Dioxido-3-oxo- 2,3-dihydro-benzisothiazol-2-yl)butyl]aminomethyl}chroman.

Hydrochloride m.p. (closed capillary): 192°–194° C.

e.e. ≧99%

$\alpha_D$=+43.5 (c=1, trichloromethane)

| $C_{21}H_{24}N_2O_4S \times HCl$ | calc. | C 57.72 | H 5.78 | N 6.41 |
|---|---|---|---|---|
| (437) | found | 57.4 | 5.72 | 6.33 |

EXAMPLE 93

(+)-2-{N-[4-(1,1-dioxido-3-oxo-2,3-dihydro-benzisothiazol-2-yl)butyl]aminomethyl)-8-methoxy-chroman and (−)-2-{N-[4-(1,1-dioxido-3-oxo-2,3-dihydro-benzisothiazol-2-yl)butyl]aminomethyl)-8-methoxy-chroman

EXAMPLE 93a

8-Methoxychroman-2-carboxylic Acid

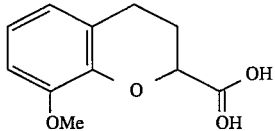

The mixture of 100.7 g (0.43 mol) 8-methoxy-2-chromancarboxylic acid ethyl ester and 20.1 g (0.50 mol) sodium hydroxide in 800 ml ethanol was stirred for 24 h at 20°. After evaporation, the residue was treated with water and extracted with diethyl ether. The aqueous phase was acidified and then extracted with diethylether. Usual work-up yielded 95.2 g of crystalline 8-methoxychroman-2-carboxylic acid.

EXAMPLE 93b

8-Methoxy-chroman-2-carbocylic Acid Chloride

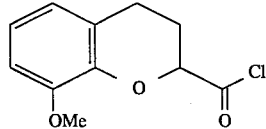

In analogy to example 92a 8-methoxy-chroman-2-carboxylic acid chloride was obtained from example 93a; it was used without further purification.

EXAMPLE 93c

8-Methoxy-N-[1-(S)-phenethyl]-chroman-2-carboxamide (Diastereomers)

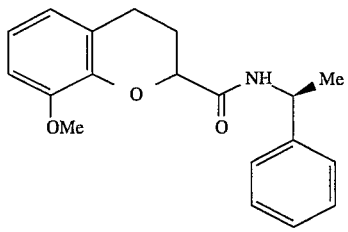

In analogy to example 92b 88.7 g (0.39 mol) 8-methoxy-chroman- 2-carboxylic acid chloride (example 93b) in 600 ml dichloromethane was reacted with 64.9 g (0.54 mol) (S)-(−)-1-phenethylamine and 54.1 g (0.54 mol) triethylamine at 10° C. Work-up provided 135.2 g crude 8-methoxy-N-[1-(S)-phenethyl]-chroman-2-carboxamide as a 1:1 mixture of diastereomers. Chromatography on 2000 g of silica with toluene/ethyl acetate provided 47.9 g pure diastereomer A and 33.9 g pure diastereomer B. 29.2 g of a mixture of these diastereomers was rechromatographed.

Diastereomer A m.p.: 123°–124° C. (dichloromethane/pet.ether)

d.e.: >99%

$\alpha_D$: +6.3° (c=1, tetrahydrofuran)

| $C_{19}H_{21}NO_3$ | calc. | C 73.29 | H 6.80 | N 4.50 |
|---|---|---|---|---|
| (311.4) | found | 73.0 | 6.69 | 4.53 |

Diastereomer B m.p.: 108°–109 ° C. (dichloromethane/pet.ether)

d.e.: 100%

$\alpha_D$: +40.2° (c=1, tetrahydrofuran)

| $C_{19}H_{21}NO_3$ | calc. | C 73.29 | H 6.80 | N 4.50 |
|---|---|---|---|---|
| (311.4) | found | 73.2 | 6.93 | 4.60 |

EXAMPLE 93d (+)-8-Methoxy-N-[1-(S)-phenethyl]-2-aminomethylchroman

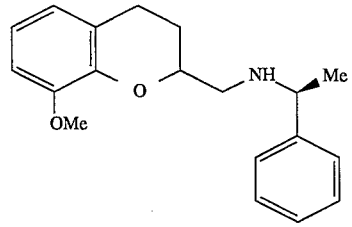

In analogy to example 92d 46.7 g (0.15 mol) 8-methoxy-N-[ 1-(S)-Phenethyl]-chroman-2-carboxamide (diastereomer A of example 93c, m.p. 123°–124° C.) in 500 ml anhydrous tetrahydrofuran was added dropwise to 0.35 mol diborane in 650 ml anhydrous tetrahydrofuran at 10° C. Work-up provided 50.8 g crude (+)-8-Methoxy-N-[1-(S)-phenethyl]-2-aminomethylchroman.

The crude products of two reactions were combined and chromatographed on silica (2000 g) with toluene/ethyl acetate (10:1 to 5:1). This gave 69.2 g of pure (+)-8-Methoxy-N-[1-(S)-phenethyl]- 2-aminomethylchroman and 21.1 g of 8-methoxy-N-[ 1-(S)-phenethyl]-chroman-2-carboxamide.

An analytical sample (1 g) was Kugelrohr-destilled;
b.p.: 160°–170° C./0.05 torr.
d.e.: 100%
$\alpha_D$: +30.2° (c=1, tetrahydrofuran)

| $C_{19}H_{23}NO_2$ (297.4) | calc. found | C 76.73 C 76.5 | H 7.80 7.84 | N 4.71 4.66 |
|---|---|---|---|---|

EXAMPLE 93e

8-Methody-N-[1-(S)-phenethyl]-2-aminomethylchroman
(Other Diastereomer)

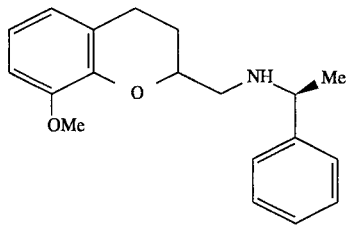

In analogy to example 93d the diastereomeric (to 93d) 8-Methoxy-N-[1-(S)-phenethyl]-2-aminomethylchroman was obtained from diastereomer B of example 93c (m.p. 108°–109° C.), d.e.: 100%.

An analytical sample was Kugelrohr-destilled;
b.p.: 175° C./0.05 torr

| $C_{19}H_{23}NO_2$ (297.4) | calc. found | C 76.73 76.8 | H 7.80 7.87 | N 4.71 5.03 |
|---|---|---|---|---|

EXAMPLE 93f (+)-2-Aminomethyl-8-methoxy-chroman

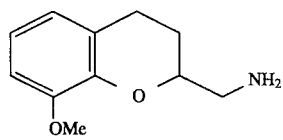

In two portions 49.2 g (0.16 mol) (+)-8-Methoxy-N-[1-(S)-phenethyl]- 2-aminomethylchroman from example 93d were hydrogenated in 400 ml ethanol (per portion) for 24 h at 50° C. and 10 bar (Pd/C 5%). Filtration and evaporation yielded 34.8 g crude 2-aminomethyl-8-methoxy-chroman, which was chromatographed on 600 g silica with toluene/ethyl acetate. The fraction eluted with toluene/ethyl acetate (1:2) was Kugelrohr-destilled at 170°–180° C./0.02 torr. This gave 20.1 g pure (+)-2-aminomethyl-8-methoxychroman.
e.e.: 96.7%

$\alpha_D$: +111.5° (c=1, trichloromethane)

| $C_{11}H_{15}NO_2$ (193.2) | calc. found | C 68.37 68.3 | H 7.82 8.02 | N 7.25 7.34 |
|---|---|---|---|---|

EXAMPLE 93c (−)-2-Aminomethyl-8-methoxy-chroman

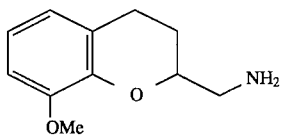

Analogously to example 93f the enantiomer to 93f was obtained from example 93e.
e.e. 96.1%
b.p.: 160°–170° C. 0.07 Torr (Kugelrohr)
melting range: 49°–55° C.
$\alpha_D$: −110.8° (c=1, trichloromethane)

| $C_{11}H_{15}NO_2$ (193.2) | calc. found | C 68.37 68.0 | H 7.82 7.88 | N 7.25 7.23 |
|---|---|---|---|---|

EXAMPLE 93h

2-{N-[4-(1,1-dioxido-3-oxo-2,3-dihydro-benzisothiazol-2-yl)butyl] aminomethyl}-8-methoxy-chroman and Its Hydrochloride [(+)-enantiomer]

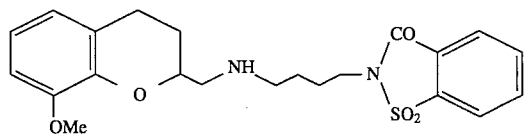

The solution of 5.3 g (0.027 mol) 2-aminomethyl-8-methoxy-chroman from example 93f, 9.5 g (0.03 mol) N-(4-bromobutyl)saccharin and 3.03 g (0.03 mol) triethylamine in 80 ml dimethylformamide was stirred for 5 h at 60° C. The mixture was evaporated in vacuo and dissolved in dichloromethane. Water was added, followed by dilute sodium hydroxide (0.1n NaOH) until pH 8 was reached. The phases were separated, the organic phase was washed with brine to pH 7 and then concentrated. This gave 17.9 g of a crude product, which was chromatographed on 250 g silica with toluene/methanol (10:1). This provided 10.5 g crude 2-(N-[4-(1,1-dioxido-3-oxo-2,3-dihydro-benzisothiazol-2-yl)butyl] aminomethyl}-8-methoxy-chroman, which was rechromatographed on 300 g silica. With toluene/methanol (10:1) 6.6 g pure product was obtained.

Hydrochloride of 93h
m.p.: 205°–208° C. (closed capillary) after recrystallization from dichloromethane/pet.ether
e.e. ≧99%

$\alpha_D$: +53.1° (c=1, trichloromethane)

| | | | | |
|---|---|---|---|---|
| $C_{22}H_{26}N_2O_5S \times HCl$ | calc. | C 56.58 | H 5.83 | N 6.00 |
| (467.0) | found | 56.8 | 5.98 | 5.97 |

EXAMPLE 93i

2-{N-[4-(1,1-dioxido-3-oxo-2,3-dihydro-benziso-thiazol-2-yl)butyl]aminomethyl}-8-methoxy-chroman and Its Hydrochloride [(−)-enantiomer]

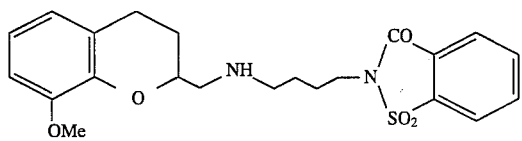

5.3 g (0.027 mol) 2-aminomethyl-8-methoxychroman from example 93g, 9.5 g (0.03 mol) N-(4-bromobutyl)saccharin, 3.05 g (0.03 mol) triethylamine and 80 ml dimethylformamide were heated to 50° C. for 4h. Work-up as described in example 93h furnished 16.6 g crude product, which was filtered through 175 g silica with toluene/ethyl acetate. This gave 3.4 g dialkylation product and 7.1 g monoalkylation product. Rechromatography of the monoalkylation product on 230 g silica with toluene/methanol (10:1) gave 2.5 g pure 2-(N-[4-(1,1-dioxido-3-oxo-2,3-dihydro-benzisothiazol- 2-yl)butyl]aminomethyl}-8-methoxy-chroman.

Hydrochloride of 93i m.p.: 208°–210° C. (closed capillary) after recrystallization from dichloromethane/pet.ether e.e.: ≧99%

$\alpha_D$: −51.2° (c=1, trichloromethane)

| | | | | |
|---|---|---|---|---|
| $C_{22}H_{26}N_2O_5S \times HCl$ | calc. | C 56.58 | H 5.83 | N 6.00 |
| (467.0) | found | 56.6 | 5.82 | 5.95 |

It will be appreciated that the instant specification and claims are set forth by way of illustration and not limitation, and that various modifications and changes may be made without departing from the spirit and scope of the present invention.

We claim:

1. A method of treating a patient prophylactically or preventively with regard to depression, which comprises administering to such patient an amount effective therefor of a substituted aminomethylchroman of the formula

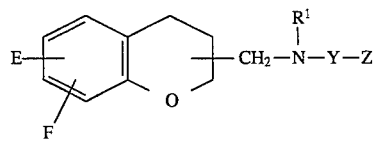

in which

Y—denotes a straight-chain or branched, saturated or unsaturated alkylene chain having up to 6 carbon atoms, Z—denotes a group of the formula

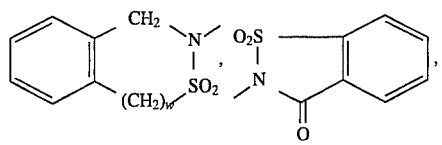

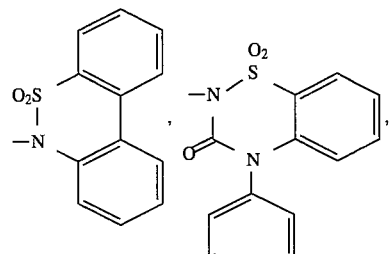

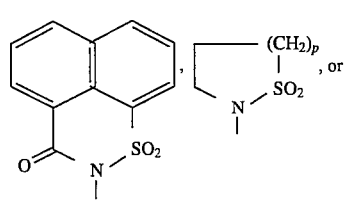

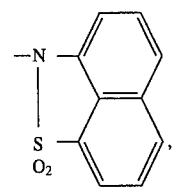

w—denotes 0, 1 or 2, p denotes 1 or 2, $R^1$—denotes hydrogen, lower alkyl or benzyl or denotes the group —($Y^1$—$Z^1$), where $Y^1$ and $Z^1$ may be identical or different to Y and Z and have the abovementioned meaning of Y and Z, E and F are identical or different and
denote hydrogen, lower alkyl or lower alkoxy or
denote fluorine, chlorine, bromine, cyano or
denote a group of the formula —$CONH_2$, or E and F together form a phenyl or cyclohexane ring or a salt thereof.

2. A method according to claim 1, wherein such compound is the (+) enantiomer of 2-{N-[4-(1,1-dioxido-3-oxo-2,3-dihydrobenzisothiazol-2-yl)-butyl]aminomethyl} chroman of the formula

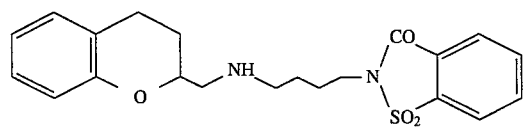

or a salt thereof.

3. A method according to claim 1, wherein such compound is the (−) enantiomer of 2-(N-[4-(1,1-dioxido-3-oxo-2,3-dihydrobenzisothiazol-2-yl)-butyl]aminomethyl} chroman of the formula

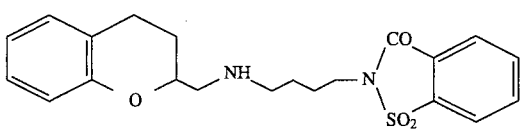

or a salt thereof.

4. A method according to claim 1, wherein such compound is the (+) enantiomer of 2-(N-[4-(1,1-dioxido-3-oxo-2,3-dihydrobenzisothiazol-2-yl)-butyl]aminomethyl}-8-methoxy chroman of the formula

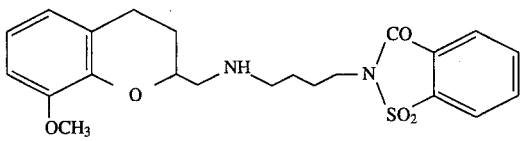

or a salt thereof.

5. A method according to claim 1, wherein such compound is the (−) enantiomer of 2-{N-[4-(1,1-dioxido-3-oxo-2,3-dihydrobenzisothiazol-2-yl)-butyl]aminomethyl)-8-methoxy chroman of the formula

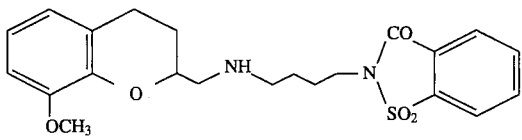

or a salt thereof.

6. A method according to claim 1, wherein such compound is 2-{N-[4-(1,1-dioxido-3-oxo-2,3-dihydrobenzisothiazol- 2-yl)butyl]aminomethyl}-8-methoxy-chroman of the formula

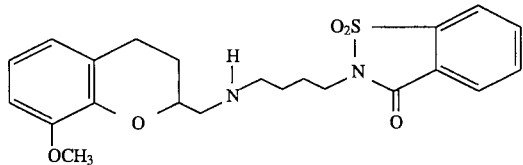

or a salt thereof.

7. A method according to claim 1, wherein such compound is 2-{N-[4-(1,1-dioxido-3-oxo-2,3-dihydrobenzisothiazol- 2-yl-butyl]aminomethyl}-5-methoxy-chroman of the formula

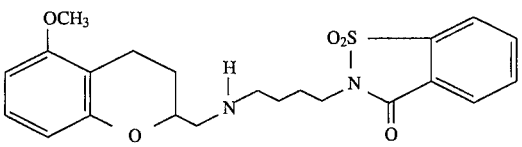

or a salt thereof.

8. A method according to claim 1, wherein such compound is 2-{N-[4(1,1-dioxido-3-oxo-2,3-dihydrobenzisothiazol- 2-yl)butyl]aminomethyl}benzo(h)chroman of the formula

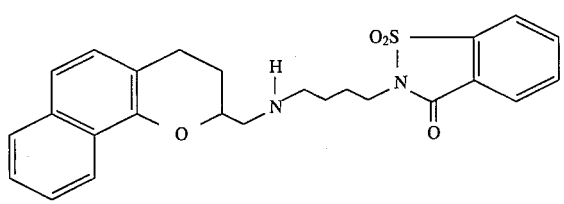

or a salt thereof.

9. A method according to claim 1, wherein such compound is 2-{N-[4-(2,3-dihydrobenzisothiazol-2-yl)butyl]}amino-methyl-8-methoxy-chroman of the formula

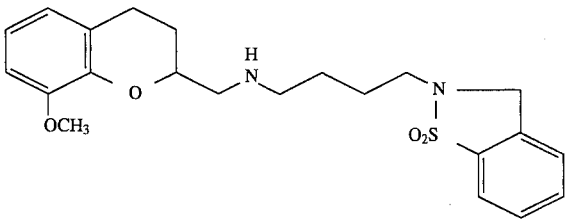

or a salt thereof.

* * * * *